United States Patent
Kimura et al.

(10) Patent No.: US 12,228,126 B2
(45) Date of Patent: Feb. 18, 2025

(54) LIQUID SUPPLY DEVICE, MICRODEVICE SYSTEM, AND LIQUID SUPPLY METHOD

(71) Applicant: HAMAMATSU PHOTONICS K.K., Hamamatsu (JP)

(72) Inventors: Yuji Kimura, Hamamatsu (JP); Hiroyasu Itoh, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 499 days.

(21) Appl. No.: 17/310,814

(22) PCT Filed: Feb. 19, 2020

(86) PCT No.: PCT/JP2020/006615
§ 371 (c)(1),
(2) Date: Aug. 25, 2021

(87) PCT Pub. No.: WO2020/175289
PCT Pub. Date: Sep. 3, 2020

(65) Prior Publication Data
US 2022/0120271 A1 Apr. 21, 2022

(30) Foreign Application Priority Data
Feb. 28, 2019 (JP) .................... 2019-036380

(51) Int. Cl.
*F04B 53/16* (2006.01)
*C12M 1/00* (2006.01)
(Continued)

(52) U.S. Cl.
CPC ............. *F04B 53/16* (2013.01); *C12M 29/00* (2013.01); *F04B 43/043* (2013.01); *F04B 53/10* (2013.01)

(58) Field of Classification Search
CPC ........ F04B 53/16; F04B 43/043; F04B 53/10; C12M 29/00
See application file for complete search history.

(56) References Cited

U.S. PATENT DOCUMENTS

2016/0199796 A1* 7/2016 Ichiki ..................... B01F 33/30
366/192

FOREIGN PATENT DOCUMENTS

| CN | 106164241 A | 11/2016 |
|---|---|---|
| JP | 2003-279569 A | 10/2003 |

(Continued)

OTHER PUBLICATIONS

Translation of JP-2008136475-A obtained Oct. 23, 2023 (Year: 2008).*

(Continued)

*Primary Examiner* — Connor J Tremarche
(74) *Attorney, Agent, or Firm* — Faegre Drinker Biddle & Reath LLP

(57) ABSTRACT

In a liquid supply device, the pump unit has a discharge port for discharging a fluid. The connecting portion is connected to the discharge port. The first and second pipe portions and branch off from the connecting portion. The first introduction unit is connected to the first pipe portion and introduces a first liquid into the first flow channel at a flow rate corresponding to a flow rate of the fluid flowing through the first pipe portion. The second introduction unit is connected to the second pipe portion and introduces a second liquid into the first flow channel at a flow rate corresponding to a flow rate of the fluid flowing through the second pipe portion. The stopping portion stops the flow of the fluid in the second pipe portion.

9 Claims, 13 Drawing Sheets

(51) Int. Cl.
  *F04B 43/04* (2006.01)
  *F04B 53/10* (2006.01)

(56) References Cited

FOREIGN PATENT DOCUMENTS

| JP | 2005-098718 | A |   | 4/2005  |          |
|----|-------------|---|---|---------|----------|
| JP | 2007-325586 | A |   | 12/2007 |          |
| JP | 2008136475  | A | * | 6/2008  | C12M 47/04 |
| JP | 2010-104918 | A |   | 5/2010  |          |
| JP | 2012-185073 | A |   | 9/2012  |          |
| JP | 2014-030382 | A |   | 2/2014  |          |
| JP | 2014038066  | A | * | 2/2014  |          |
| JP | 2015-002684 | A |   | 1/2015  |          |

OTHER PUBLICATIONS

English Translation of JP-2014038066-A obtained Feb. 7, 2023 (Year: 2014).*
International Preliminary Report on Patentability mailed Sep. 10, 2021 for PCT/JP2020/006615.

* cited by examiner

LIQUID SUPPLY DEVICE, MICRODEVICE SYSTEM, AND LIQUID SUPPLY METHOD

TECHNICAL FIELD

The present invention relates to a liquid supply device, a microdevice system, and a liquid supply method.

BACKGROUND ART

A known microdevice system includes a microfluidic device and a liquid supply device supplying a liquid to the microfluidic device(for example, Patent Literature 1). In the microfluidic device disclosed in Patent Literature 1, two flow channels run along each other. A communication hole allows the two flow channels to communicate with each other. A desired liquid is supplied to each of the two flow channels. The microfluidic device is made by, for example, MEMS technology.

CITATION LIST

Patent Literature

Patent Literature 1: Japanese Unexamined Patent Publication No. 2015-002684

SUMMARY OF INVENTION

Technical Problem

The microfluidic device includes, for example, a device forming a lipid bilayer membrane in the communication hole or a device capturing a cell on one flow channel side of the communication hole by using the pressure difference between the two flow channels. As for the microfluidic device, it is conceivable to introduce a plurality of types of liquids into one flow channel at any timing. For example, it is conceivable to simultaneously introduce two types of liquids into a first flow channel and then stop the introduction of one of the two types of liquids introduced in the first flow channel in a state where a liquid is introduced in a second flow channel.

In this case, when the flow rate of the liquid flowing through the first flow channel changes as the liquid introduction into the first flow channel is stopped, the pressure of the first flow channel also changes. When the pressure of the first flow channel changes abruptly, a problem arises in the form of an abrupt change in the pressure difference between the first flow channel and the second flow channel The change in the pressure difference between the two flow channels affects the object that is positioned in the communication hole. When a lipid membrane is formed in the communication hole, for example, the formed lipid membrane may be crushed due to the change in pressure difference. When a cell is disposed in the communication hole, for example, the cell may be unintentionally detached from the communication hole or the cell may be pressed against the communication hole and crushed, due to the change in pressure difference.

Conceivable in order to solve the above problem is that the liquid supply device supplying the liquid to the microfluidic device electronically controls the amount of introduction of the liquid introduced into each flow channel depending on the situation. However, this may lead to an increase in size, complexity, and cost of the liquid supply device.

One aspect of the present invention is to provide a liquid supply device capable of suppressing a change in inter-flow channel pressure difference with a simple configuration. Another aspect of the present invention is to provide a microdevice system capable of suppressing a change in inter-flow channel pressure difference with a simple configuration. Yet another aspect of the present invention is to provide a liquid supply method capable of suppressing a change in inter-flow channel pressure difference with a simple configuration.

Solution to Problem

A liquid supply device according to one aspect of the present invention is arranged to supply a liquid to a microfluidic device having a first flow channel, a second flow channel, and a communication hole. The second flow channel runs along the first flow channel The communication hole allows the first flow channel and the second flow channel to communicate with each other. The liquid supply device includes a pump unit, a branch pipe, a first introduction unit, a second introduction unit, and a stopping portion. The pump unit has a discharge port for discharging a fluid. The branch pipe has a connecting portion and first and second pipe portions. The connecting portion is connected to the discharge port. The first and second pipe portions branch off from the connecting portion. The first introduction unit is connected to the first pipe portion and is arranged to introduce a first liquid into the first flow channel at a flow rate corresponding to a flow rate of the fluid flowing through the first pipe portion. The second introduction unit is connected to the second pipe portion and is arranged to introduce a second liquid into the first flow channel at a flow rate corresponding to a flow rate of the fluid flowing through the second pipe portion. The stopping portion is arranged to stop the flow of the fluid in the second pipe portion.

In this aspect, the second introduction unit is arranged to introduce the second liquid into the first flow channel at a flow rate corresponding to the flow rate of the fluid flowing through the second pipe portion. Accordingly, the introduction of the second liquid into the first flow channel is stopped by the flow of the fluid in the second pipe portion being stopped. In a state where the flow of the fluid in the second pipe portion is stopped, the fluid discharged from the discharge port of the pump unit flows into a part of the branch pipe other than the second pipe portion. In the branch pipe, the first and second pipe portions branch off from the connecting portion, and thus the flow rate of the fluid in the first pipe portion in the state where the flow of the fluid in the second pipe portion is stopped increases as compared with a state where the flow of the fluid in the second pipe portion is not stopped. The first introduction unit is arranged to introduce the first liquid into the first flow channel at a flow rate corresponding to the flow rate of the fluid flowing through the first pipe portion. Accordingly, a change in the flow rate of the liquid flowing through the first flow channel is suppressed even in the case of transition between the state where the flow of the fluid in the second pipe portion is stopped and the state where the flow of the fluid in the second pipe portion is not stopped. Accordingly, in the liquid supply device, a change in pressure in the first flow channel is suppressed even in the case of transition between a case where the flow of the fluid in the second pipe portion is stopped and a case where the flow of the fluid in the second pipe portion is not stopped. As a result, it is possible to suppress a change in the pressure difference between the first flow channel and the second flow channel with a simple configuration and without electronically controlling the amounts of introduction of the first and second liquids.

In this aspect, the first introduction unit may include a first containing pipe connected to the first pipe portion and arranged to contain the first liquid inside. The second introduction unit may include a second containing pipe connected to the second pipe portion and arranged to contain the second liquid inside. In this case, the first liquid contained in the first containing pipe is pushed out in accordance with the flow rate of the fluid flowing through the first pipe portion. The second liquid contained in the second containing pipe is pushed out in accordance with the flow rate of the fluid flowing through the second pipe portion. As a result, it is possible to suppress a change in the pressure difference between the first flow channel and the second flow channel with a simpler configuration.

In this aspect, the stopping portion may include a valve arranged to open and close a flow channel connecting the second pipe portion and the second introduction unit. In this case, the flow of the fluid in the second pipe portion can be easily stopped by the valve. Insofar as the valve is provided between the second introduction unit and the second pipe portion, the fluid from the pump unit flows into a part of the branch pipe other than the second pipe portion without being affected by the compressibility of the second liquid, flow channel expansion in the second introduction unit, and so on when the flow of the fluid of the second pipe portion is stopped by the valve. Accordingly, a change in pressure in the first flow channel is further suppressed.

A microdevice system according to another aspect of the present invention includes a microfluidic device, a first supply unit, and a second supply unit. The microfluidic device has a first flow channel, a second flow channel, and a communication hole. The second flow channel runs along the first flow channel. The communication hole allows the first flow channel and the second flow channel to communicate with each other. The first supply unit is arranged to supply a liquid to the first flow channel The second supply unit is arranged to supply a liquid to the second flow channel. The first supply unit includes a pump unit, a branch pipe, a first introduction unit, a second introduction unit, and a stopping portion. The pump unit has a discharge port for discharging a fluid. The branch pipe has a connecting portion and first and second pipe portions. The connecting portion is connected to the discharge port of the pump unit of the first supply unit. The first and second pipe portions branch off from the connecting portion. The first introduction unit is connected to the first pipe portion and arranged to introduce a first liquid into the first flow channel at a flow rate corresponding to a flow rate of the fluid flowing through the first pipe portion. The second introduction unit is connected to the second pipe portion and arranged to introduce a second liquid into the first flow channel at a flow rate corresponding to a flow rate of the fluid flowing through the second pipe portion. The stopping portion is arranged to stop the flow of the fluid in the second pipe portion.

In this aspect, the second introduction unit is arranged to introduce the second liquid into the first flow channel at a flow rate corresponding to the flow rate of the fluid flowing through the second pipe portion. Accordingly, the introduction of the second liquid into the first flow channel is stopped by the flow of the fluid in the second pipe portion being stopped. In a state where the flow of the fluid in the second pipe portion is stopped, the fluid discharged from the discharge port of the pump unit flows into a part of the branch pipe other than the second pipe portion. In the branch pipe, the first and second pipe portions branch off from the connecting portion, and thus the flow rate of the fluid in the first pipe portion in the state where the flow of the fluid in the second pipe portion is stopped increases as compared with a state where the flow of the fluid in the second pipe portion is not stopped. The first introduction unit is arranged to introduce the first liquid into the first flow channel at a flow rate corresponding to the flow rate of the fluid flowing through the first pipe portion. Accordingly, a change in the flow rate of the liquid flowing through the first flow channel is suppressed even in the case of transition between the state where the flow of the fluid in the second pipe portion is stopped and the state where the flow of the fluid in the second pipe portion is not stopped. Accordingly, in the microdevice system, a change in pressure in the first flow channel is suppressed even in the case of transition between the state where the flow of the fluid in the second pipe portion is stopped and the state where the flow of the fluid in the second pipe portion is not stopped. As a result, it is possible to suppress a change in the pressure difference between the first flow channel and the second flow channel with a simple configuration and without electronically controlling the amounts of introduction of the first and second liquids.

In this aspect, the microfluidic device may have first and second inflow channels connected to the first flow channel The first and second inflow channels may be disposed at positions farther from the second flow channel than the communication hole in a direction orthogonal to an extension direction of the second flow channel on a plane passing through the first flow channel and the second flow channel. The second inflow channel may run closer to the second flow channel side than the first inflow channel when viewed in a direction orthogonal to the plane. The first introduction unit may be disposed so as to introduce the first liquid into the first inflow channel. The second introduction unit may be disposed so as to introduce the second liquid into the second inflow channel In this case, a layer through which the first liquid flows and a layer through which the second liquid flows are formed in the first flow channel by the first and second liquids being introduced into the first and second inflow channels, respectively. With this configuration, it is possible to control the liquid supplied to the communication hole depending on whether or not the second liquid is introduced into the second inflow channel.

In this aspect, the second supply unit may include a pump unit, a branch pipe, a third introduction unit, a fourth introduction unit, and a stopping portion. The pump unit may have a discharge port for discharging a fluid. The branch pipe may have a connecting portion and third and fourth pipe portions. The connecting portion may be connected to the discharge port of the pump unit of the second supply unit. The third and fourth pipe portions may branch off from the connecting portion. The third introduction unit may be connected to the third pipe portion and be arranged to introduce a third liquid into the second flow channel at a flow rate corresponding to a flow rate of the fluid flowing through the third pipe portion. The fourth introduction unit may be connected to the fourth pipe portion and be arranged to introduce a fourth liquid into the second flow channel at a flow rate corresponding to a flow rate of the fluid flowing through the fourth pipe portion. The stopping portion may be arranged to stop the flow of the fluid in the third pipe portion. In this case, the second supply unit is similar in configuration to the first supply unit. Accordingly, a change in pressure in the second flow channel is suppressed even in the case of transition between a state where the flow of the fluid in the third pipe portion is stopped and a state where the flow of the fluid in the third pipe portion is not stopped. As a result, it is possible to suppress a change in the pressure difference between the first flow channel and the second flow channel with a simple configuration and without electronically controlling the amounts of introduction of the first, second, third, and fourth liquids.

In this aspect, the microfluidic device may have third and fourth inflow channels connected to the second flow channel. The third and fourth inflow channels may be disposed at positions farther from the first flow channel than the communication hole in a direction orthogonal to the extension direction of the second flow channel on a plane passing through the first flow channel and the second flow channel The third inflow channel may run closer to the first flow channel side than the fourth inflow channel when viewed in a direction orthogonal to the plane. The third introduction unit may be disposed so as to introduce the third liquid into the third inflow channel The fourth introduction unit may be disposed so as to introduce the fourth liquid into the fourth inflow channel. In this case, a layer through which the third liquid flows and a layer through which the fourth liquid flows are formed in the second flow channel by the third and fourth liquids being introduced into the third and fourth inflow channels, respectively. With this configuration, it is possible to control the liquid supplied to the communication hole depending on whether or not the third liquid is introduced.

In this aspect, a diameter of the communication hole may be 1 to 15 µm. In this case, a cell can be captured by the communication hole by a pressure difference being provided between the first flow channel and the second flow channel.

By a liquid supply method according to yet another aspect of the present invention, a liquid is supplied to a microfluidic device having a first flow channel, a second flow channel, and a communication hole. The second flow channel runs along the first flow channel The communication hole allows the first flow channel and the second flow channel to communicate with each other. The liquid supply method includes a step of preparing a liquid supply device supplying a liquid to a microfluidic device and a step of introducing a liquid into the first flow channel and the second flow channel by using the liquid supply device. The liquid supply device has a first supply unit arranged to supply a liquid to the first flow channel and a second supply unit arranged to supply a liquid to the second flow channel. The first supply unit includes a pump unit, a branch pipe, a first introduction unit, and a second introduction unit. The pump unit has a discharge port for discharging a fluid. The branch pipe has a connecting portion and first and second pipe portions. The connecting portion is connected to the discharge port. The first and second pipe portions branch off from the connecting portion. The first introduction unit is connected to the first pipe portion and is arranged to introduce a first liquid into the first flow channel at a flow rate corresponding to a flow rate of the fluid flowing through the first pipe portion. The second introduction unit is connected to the second pipe portion and is arranged to introduce a second liquid into the first flow channel at a flow rate corresponding to a flow rate of the fluid flowing through the second pipe portion. The step of supplying the liquid includes a step of discharging the fluid from the discharge port of the pump unit of the first supply unit and causing the fluid to flow into the first and second pipe portions and a step of stopping the flow of the fluid in the second pipe portion while causing the fluid to flow into the first pipe portion after the step of causing the fluid to flow into the first and second pipe portions.

In this aspect, the first and second liquids are introduced into the first flow channel in the step of causing the fluid to flow into the first and second pipe portions. In the step of stopping the flow of the fluid in the second pipe portion, the first liquid is introduced into the first flow channel without the second liquid being introduced. In a state where the flow of the fluid in the second pipe portion is stopped, the fluid discharged from the discharge port of the pump unit flows into a part of the branch pipe other than the second pipe portion. Accordingly, the flow rate of the fluid in the first pipe portion in the state where the flow of the fluid in the second pipe portion is stopped increases as compared with a state where the flow of the fluid in the second pipe portion is not stopped. Accordingly, a change in the flow rate of the liquid flowing through the first flow channel is suppressed even in the case of transition between the state where the flow of the fluid in the second pipe portion is stopped and the state where the flow of the fluid in the second pipe portion is not stopped. Accordingly, in the liquid supply method, a change in pressure in the first flow channel is suppressed between the step of causing the fluid to flow into the first and second pipe portions and the step of stopping the flow of the fluid in the second pipe portion. As a result, it is possible to suppress a change in the pressure difference between the first flow channel and the second flow channel with a simple configuration and without electronically controlling the amounts of introduction of the first and second liquids.

In this aspect, in the step of causing the fluid to flow into the first and second pipe portions, the first liquid and the second liquid may be caused to flow in parallel such that the second liquid flows closer to the second flow channel than the first liquid in the first flow channel. In this case, the liquid supplied to the communication hole can be controlled between the step of causing the fluid to flow into the first and second pipe portions and the step of stopping the flow of the fluid in the second pipe portion.

In this aspect, the second supply unit may include a pump unit, a branch pipe, a third introduction unit, and a fourth introduction unit. The pump unit may have a discharge port for discharging a fluid. The branch pipe may have a connecting portion and third and fourth pipe portions. The connecting portion may be connected to the discharge port. The third and fourth pipe portions may branch off from the connecting portion. The third introduction unit may be connected to the third pipe portion and introduce a third liquid into the second flow channel at a flow rate corresponding to a flow rate of the fluid flowing through the third pipe portion. The fourth introduction unit may be connected to the fourth pipe portion and introduce a fourth liquid into the second flow channel at a flow rate corresponding to a flow rate of the fluid flowing through the fourth pipe portion. The step of supplying the liquid may include a step of discharging the fluid from the discharge port of the pump unit of the second supply unit and causing the fluid to flow into the third and fourth pipe portions and a step of stopping the flow of the fluid in the third pipe portion while causing the fluid to flow into the fourth pipe portion after the step of causing the fluid to flow into the third and fourth pipe portions. In this case, the third and fourth liquids are introduced into the second flow channel in the step of causing the fluid to flow into the third and fourth pipe portions. In the step of stopping the flow of the fluid in the third pipe portion, the fourth liquid is introduced into the second flow channel without the third liquid being introduced. In a state where the flow of the fluid in the third pipe portion is stopped, the fluid discharged from the discharge port of the pump unit flows into a part of the branch pipe other than the third pipe portion. Accordingly, the flow rate of the fluid in the fourth pipe portion in the state where the flow of the fluid in the third pipe portion is stopped increases as compared with a state where the flow of the fluid in the third pipe portion is not stopped. Accordingly, in the liquid supply method, a change in pressure in the second flow channel is suppressed between the step of causing the fluid to flow into the third and fourth pipe portions and the step of stopping the flow of the fluid in the third pipe portion. As a result, it is possible to suppress a change in the pressure difference between the first flow channel and the second flow channel with a simple configuration and without electronically controlling the amounts of introduction of the first, second, third, and fourth liquids.

In this aspect, in the step of causing the fluid to flow into the third and fourth pipe portions, the third liquid and the fourth liquid may be caused to flow in parallel such that the third liquid flows closer to the first flow channel than the fourth liquid in the second flow channel. In this case, the liquid supplied to the communication hole can be controlled between the step of causing the fluid to flow into the third and fourth pipe portions and the step of stopping the flow of the fluid in the third pipe portion.

In this aspect, the second liquid may be a suspension containing a plurality of cells. The fourth liquid may be a sample containing a target substance to be brought into contact with a cell. In the step of causing the fluid to flow into the first and second pipe portions and the step of causing the fluid to flow into the third and fourth pipe portions, the fluid may be discharged from the pump unit of the first supply unit and the pump unit of the second supply unit such that pressure in the first flow channel becomes higher than pressure in the second flow channel. A flow rate of the fluid discharged by the pump unit of the first supply unit and a flow rate of the fluid discharged by the pump unit of the second supply unit in the step of causing the fluid to flow into the first and second pipe portions and the step of causing the fluid to flow into the third and fourth pipe portions may be maintained in the step of stopping the flow of the fluid in the second pipe portion. In this case, a cell can be captured on the first flow channel side of the communication hole. In the step of stopping the flow of the fluid in the third pipe portion, the target substance is capable of being brought into contact with the captured cell. In the step of stopping the flow of the fluid in the second pipe portion, a change in the pressure difference between the first flow channel and the second flow channel is suppressed. Accordingly, the captured cell is prevented from being unintentionally detached from the communication hole and the captured cell is prevented from being pressed against the communication hole and crushed.

In this aspect, the flow rate of the fluid discharged by the pump unit of the first supply unit and the flow rate of the fluid discharged by the pump unit of the second supply unit in the step of causing the fluid to flow into the first and second pipe portions and the step of causing the fluid to flow into the third and fourth pipe portions may be maintained in the step of stopping the flow of the fluid in the third pipe portion. In this case, a change in the pressure difference between the first flow channel and the second flow channel is suppressed in the step of stopping the flow of the fluid in the third pipe portion. Accordingly, the captured cell is prevented from being unintentionally detached from the communication hole and the captured cell is prevented from being pressed against the communication hole and crushed.

In this aspect, the first liquid may be an aqueous solution. The second liquid may be a lipid-dissolved oily solution. The step of supplying the liquid may include a step of supplying an aqueous solution to the second flow channel before the step of stopping the flow of the fluid in the second pipe portion. In the step of causing the fluid to flow into the first and second pipe portions and the step of supplying the aqueous solution to the second flow channel, the fluid may be discharged from the pump unit of the first supply unit and the pump unit of the second supply unit such that pressure in the first flow channel and pressure in the second flow channel become equal to each other. A flow rate of the fluid discharged by the pump unit of the first supply unit and a flow rate of the fluid discharged by the pump unit of the second supply unit in the step of causing the fluid to flow into the first and second pipe portions and the step of supplying the aqueous solution to the second flow channel may be maintained in the step of stopping the flow of the fluid in the second pipe portion. In this case, a single molecule lipid membrane is formed in the communication hole before the flow of the fluid in the second pipe portion is stopped and a lipid bilayer membrane is formed in the communication hole in the step of stopping the flow of the fluid in the second pipe portion. A change in the pressure difference between the first flow channel and the second flow channel is suppressed in the step of stopping the flow of the fluid in the second pipe portion. Accordingly, the formed lipid membrane is prevented from being crushed.

Advantageous Effects of Invention

According to one aspect of the present invention, it is possible to provide a liquid supply device capable of suppressing a change in inter-flow channel pressure difference with a simple configuration. According to another aspect of the present invention, it is possible to provide a microdevice system capable of suppressing a change in inter-flow channel pressure difference with a simple configuration. According to yet another aspect of the present invention, it is possible to provide a liquid supply method capable of suppressing a change in inter-flow channel pressure difference with a simple configuration.

DESCRIPTION OF EMBODIMENTS

Figure 1:
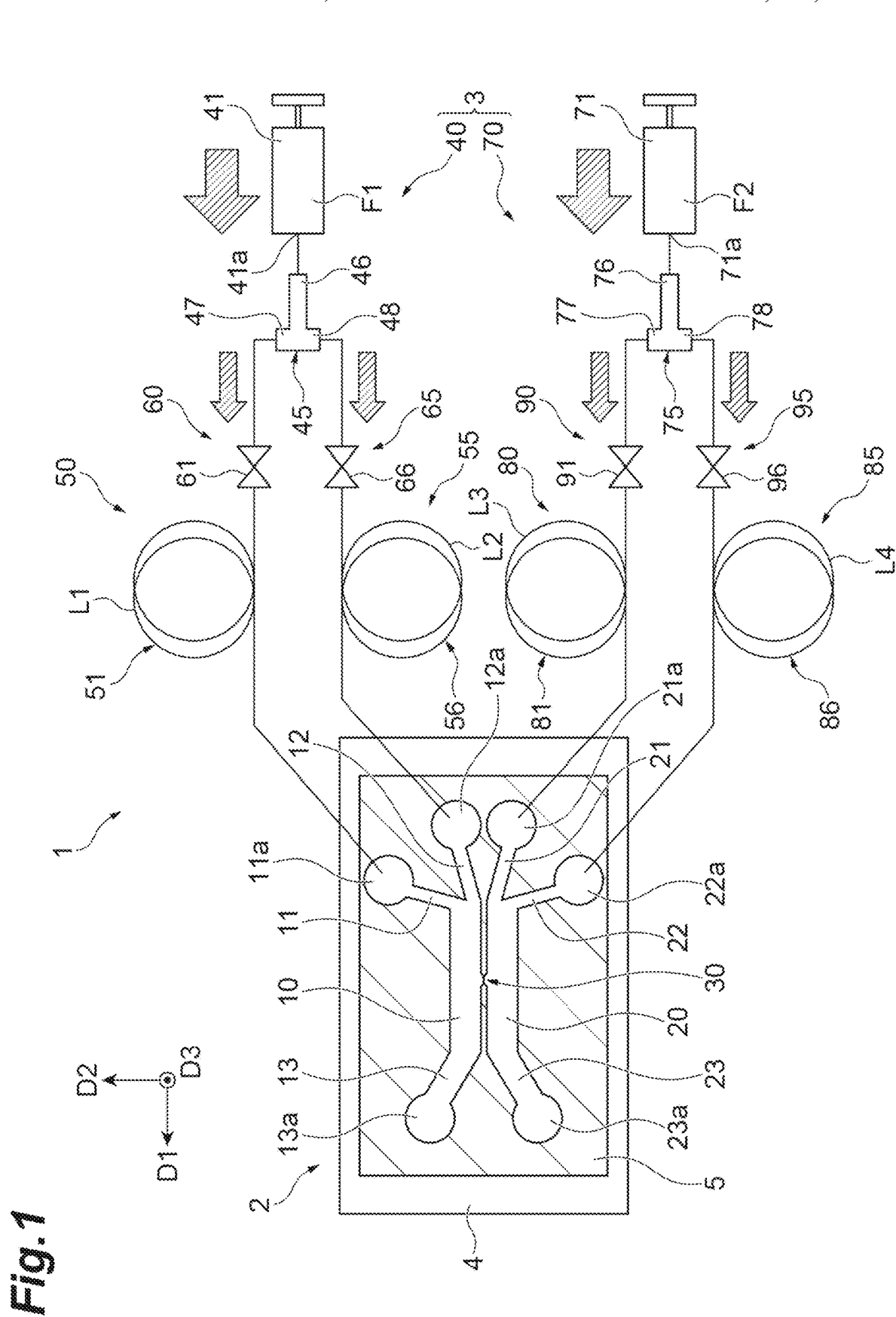
FIG. 1 is a schematic diagram of a microdevice system according to the present embodiment.

Hereinafter, an embodiment of the present invention will be described in detail with reference to the accompanying drawings. It should be noted that the same reference numerals will be used for the same elements or elements having the same functions in the following description and redundant description will be omitted.

Figure 2:
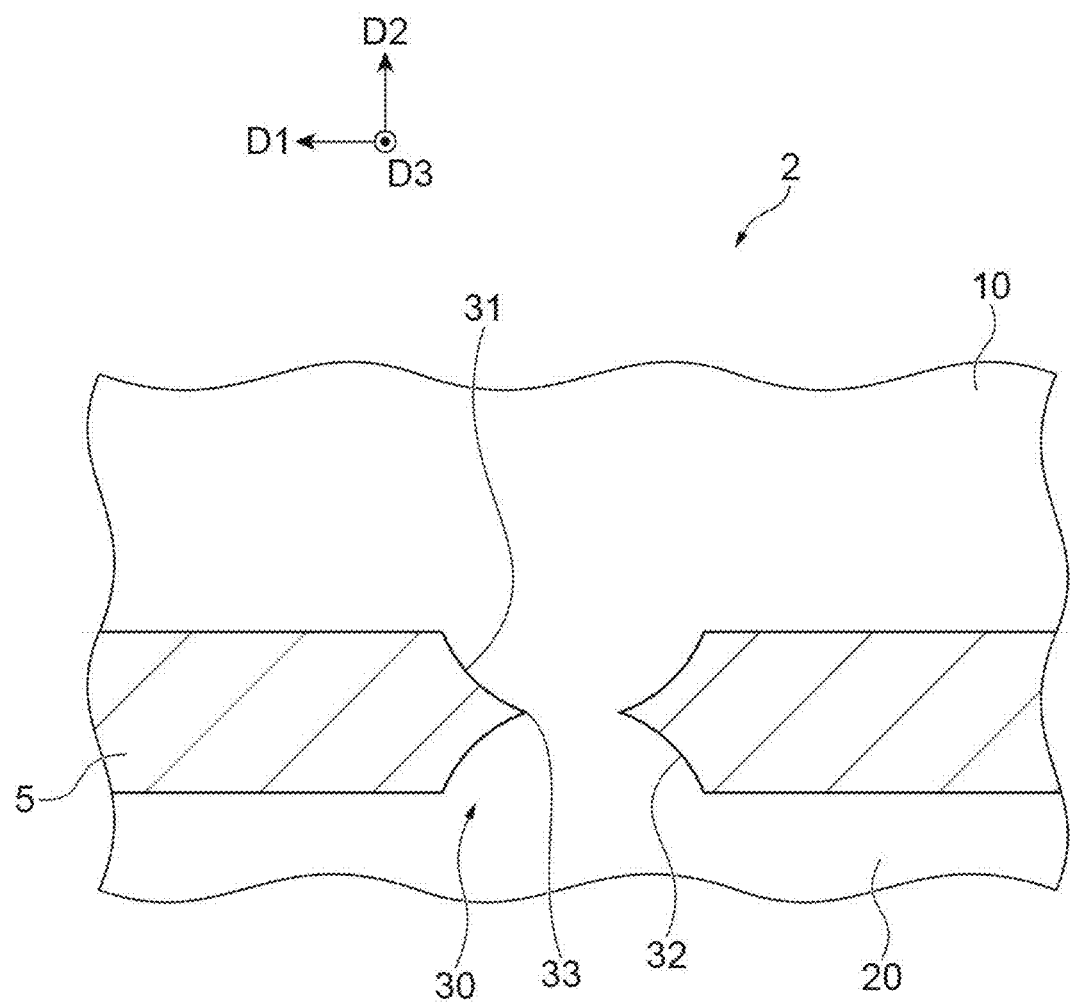
FIG. 2 is a partially enlarged view of a microfluidic device.

First, a microdevice system according to the present embodiment will be described with reference to FIGS. 1 and 2. FIG. 1 is a schematic diagram of a microdevice system. FIG. 2 is a partially enlarged view of a microfluidic device. A microdevice system 1 is used for observing a reaction of a captured cell to a target substance, forming a lipid bilayer membrane, or the like. The microdevice system 1 is, for example, a microfluidic device or a nanofluidic device.

The microdevice system 1 includes a microfluidic device 2 and a liquid supply device 3. The liquid supply device 3 supplies a desired liquid to the microfluidic device 2. In the present embodiment, the liquid supply device 3 supplies four types of liquids L1, L2, L3, and L4 to the microfluidic device 2. For example, the liquid L1 is a first liquid, the liquid L2 is a second liquid, the liquid L3 is a third liquid, and the liquid L4 is a fourth liquid.

The microfluidic device 2 includes cover glass 4 and a substrate 5. The substrate 5 is stacked on the cover glass 4. The substrate 5 has a pair of main surfaces. As illustrated in FIG. 1, the substrate 5 is provided with a groove where the liquid supplied from the liquid supply device 3 flows. FIG. 1 illustrates a cross section parallel to the pair of main surfaces of the substrate 5. The substrate 5 is in contact with the cover glass 4 on one of the main surfaces. The substrate 5 is formed of, for example, resin such as silicon rubber. Examples of the material of the silicon rubber include dimethylpolysiloxane. The groove of the substrate 5 is formed by, for example, photolithography or the like.

The groove provided in the substrate 5 includes a pair of flow channels 10 and 20, inflow channels 11, 12, 21, and 22, outflow channels 13 and 23, and a communication portion 30. The flow channels 10 and 20 have one end and the other end. One end of the flow channels 10 and 20 constitutes a flow channel inlet. The other end of the flow channels 10 and 20 constitutes a flow channel outlet. The inflow channels 11 and 12 are connected to one end of the flow channel 10. The outflow channel 13 is connected to the other end of the flow channel 10. The inflow channels 21 and 22 are connected to one end of the flow channel 20. The outflow channel 23 is connected to the other end of the flow channel 20. The communication portion 30 allows the flow channel 10 and the flow channel 20 to communicate with each other in the region between one end and the other end of the flow channels 10 and 20.

The pair of flow channels 10 and 20 run along each other in a direction D1 in parallel to the main surface of the substrate 5. In other words, the pair of flow channels 10 and 20 pass through a plane parallel to the main surface of the substrate 5 and are arranged in a direction D2 orthogonal to the direction D1 on the plane. The flow channel 10 and the flow channel 20 are partitioned by the wall that is positioned between the flow channel 10 and the flow channel 20. In the present embodiment, the flow channels 10 and 20 are linear. The flow channels 10 and 20 may be arcuate.

In the present embodiment, the width of the wall between the flow channel 10 and the flow channel 20 is smaller than the width of the flow channels 10 and 20 when viewed in a direction D3 orthogonal to the main surface of the substrate 5. In the present embodiment, the flow channels 10 and 20 have a rectangular cross section and the cross-sectional area of the flow channel 10 and the cross-sectional area of the flow channel 20 are equal to each other. The flow channel 10 and the flow channel 20 also have the same cross-sectional shape. For example, the flow channel 20 is a second flow channel when the flow channel 10 is a first flow channel. For example, in the present embodiment, the inflow channel 11 is a first inflow channel, the inflow channel 12 is a second inflow channel, the inflow channel 21 is a third inflow channel, and the inflow channel 22 is a fourth inflow channel.

The width of the flow channels 10 and 20 in the direction D2 is, for example, 100 µm. The width of the flow channels 10 and 20 in the direction D2 may be 50 µm to 2,000 µm. The length of the flow channels 10 and 20 is, for example, 7 mm The depth of the flow channels 10 and 20 in the direction D3 is, for example, 25 µm. The depth of the flow channels 10 and 20 in the direction D3 may be 15 µm to 30 µm.

As illustrated in FIG. 2, the communication portion 30 includes a recess 31 provided in the flow channel 10, a recess 32 provided in the flow channel 20, and a communication hole 33 allowing the recess 31 and the recess 32 to communicate with each other. The recess 31 has a U shape recessed toward the flow channel 20 side when viewed in the direction D3. The recess 32 has a U shape recessed toward the flow channel 10 side when viewed in the direction D3. The communication hole 33 penetrates the bottom surfaces of the U-shaped recesses 31 and 32 and allows the flow channel 10 and the flow channel 20 to communicate with each other. The communication hole 33 is provided in the direction D2.

The inflow channels 11 and 12 and the outflow channel 13 have one end and the other end. One end of the inflow channel 11 includes an injection port 11a. The other end of the inflow channel 11 is connected to the flow channel 10. One end of the inflow channel 12 includes an injection port 12a. The other end of the inflow channel 12 is connected to the flow channel 10. One end of the outflow channel 13 includes an outflow port 13a. The other end of the outflow channel 13 is connected to the flow channel 10.

The inflow channels 11 and 12 and the outflow channel 13 are provided at positions farther from the flow channel 20 than the communication hole 33 in the direction D2. The inflow channels 11 and 12 and the outflow channel 13 are linear. The inflow channel 12 runs closer to the flow channel 20 side than the inflow channel 11 when viewed in the direction D3. In the present embodiment, the inflow channels 11 and 12 and the outflow channel 13 run in a direction parallel to the main surface of the substrate 5 and intersecting with an extension direction D1 of the flow channels 10 and 20. The inflow channel 11 is inclined with respect to the extension direction D1 of the flow channels 10 and 20 at an angle larger than that of the inflow channel 12.

The inflow channels 21 and 22 and the outflow channel 23 have one end and the other end. One end of the inflow channel 21 includes an injection port 21a. The other end of the inflow channel 21 is connected to the flow channel 20. One end of the inflow channel 22 includes an injection port 22a. The other end of the inflow channel 22 is connected to the flow channel 20. One end of the outflow channel 23 includes an outflow port 23a. The other end of the outflow channel 23 is connected to the flow channel 20.

The inflow channels 21 and 22 and the outflow channel 23 are provided at positions farther from the flow channel 10 than the communication hole 33 in the direction D2. In the present embodiment, the inflow channels 21 and 22 and the outflow channel 23 are linear. The inflow channel 21 runs closer to the flow channel 10 side than the inflow channel 22 when viewed in the direction D3. In the present embodiment, the inflow channels 21 and 22 and the outflow channel 23 run in a direction parallel to the main surface of the substrate 5 and intersecting with the extension direction D1 of the flow channels 10 and 20. The inflow channel 22 is inclined with respect to the extension direction D1 of the flow channels 10 and 20 at an angle larger than that of the inflow channel 21. The inflow channel 21 may run in the extension direction D1 of the flow channels 10 and 20.

The liquid supply device 3 includes a supply unit 40 supplying a liquid to the flow channel 10 and a supply unit 70 supplying a liquid to the flow channel 20. The supply unit 40 includes a pump unit 41, a branch pipe 45, introduction units 50 and 55, and stopping portions 60 and 65. The supply unit 70 includes a pump unit 71, a branch pipe 75, introduction units 80 and 85, and stopping portions 90 and 95. For example, in the present embodiment, the introduction unit 50 is a first introduction unit, the introduction unit 55 is a second introduction unit, the introduction unit 80 is a third introduction unit, and the introduction unit 85 is a fourth introduction unit. For example, the supply unit 40 is a first supply unit and the supply unit 70 is a second supply unit.

The pump unit 41 has a discharge port 41a for discharging a fluid F1. The pump unit 41 is, for example, a syringe pump containing the fluid F1 discharged from the discharge port 41a. The pump unit 41 may manually discharge the fluid F1 from the discharge port 41a. The pump unit 41 discharges the fluid F1 from the discharge port 41a at a constant flow rate. The fluid F1 is, for example, a first fluid.

The fluid F1 discharged from the discharge port 41a by the pump unit 41 is, for example, an incompressible fluid. Examples of the incompressible fluid include a liquid. Examples of the liquid include a buffer solution. The buffer solution may be, for example, phosphate buffered saline (hereinafter, referred to as "PBS"). In FIG. 1, the arrow that is illustrated with respect to the supply unit 40 indicates the flow rate of the fluid F1. In FIG. 1, the arrow that is illustrated with respect to the supply unit 70 indicates the flow rate of a fluid F2. The wider the arrow, the higher the flow rate. It should be noted that "flow rate" is a volumetric flow rate and means a volume per unit time of fluid movement.

The branch pipe 45 has a connecting portion 46 and a plurality of pipe portions 47 and 48. In the present embodiment, the branch pipe 45 has two pipe portions 47 and 48. The connecting portion 46 is connected to the discharge port 41a. The fluid F1 discharged from the discharge port 41a flows into the branch pipe 45 from the connecting portion 46. In the present embodiment, the syringe pump and the connecting portion 46 of the branch pipe 45 are connected by a silicone tube.

The pipe portions 47 and 48 branch off from the connecting portion 46. Accordingly, the fluid F1 that has flowed in from the connecting portion 46 flows into at least one of the plurality of pipe portions 47 and 48. The flow rate of the fluid F1 flowing into the connecting portion 46 after the branch pipe 45 is filled with the fluid F1 is the total flow rate of the fluid F1 flowing out of the pipe portions 47 and 48. Although the branch pipe 45 branches off from the connecting portion 46 into the two pipe portions 47 and 48 in the present embodiment, it may branch into three or more pipe portions 47 and 48.

The introduction unit 50 introduces the liquid L1 into the flow channel 10. The introduction unit 50 is disposed so as to introduce the liquid L1 into the injection port 11a of the inflow channel 11. The introduction unit 50 has a configuration for containing the liquid L1. In the present embodiment, the introduction unit 50 includes an containing pipe 51 in which the liquid L1 is contained. One end of the containing pipe 51 is connected to the pipe portion 47. The other end of the containing pipe 51 is disposed at the injection port 11a of the microfluidic device 2. The containing pipe 51 has a sufficient length in accordance with the volume of the liquid L1 to be contained. The containing pipe 51 is configured in a loop shape in order to save space. In the present embodiment, the introduction unit 50 contains the liquid L1 in the containing pipe 51 and the volume of the contained liquid L1 exceeds the volume of the flow channel 10 from the connection position between the inflow channel 11 and the flow channel 10 to the connection position between the flow channel 10 and the communication hole 33 in the extension direction D1. For example, the containing pipe 51 is a first containing pipe.

The fluid F1 that has flowed out of the pipe portion 47 flows into the containing pipe 51. As a result, the liquid L1 contained in the containing pipe 51 is pushed out by the fluid F1 that has flowed into the containing pipe 51. Specifically, the liquid L1 contained in the containing pipe 51 moves to the side opposite to the pipe portion 47 in accordance with the volume of the fluid F1 that has flowed into the containing pipe 51. Accordingly, the flow rate of the liquid L1 supplied from the containing pipe 51 to the flow channel 10 of the microfluidic device 2 is the flow rate of the fluid F1 flowing out of the pipe portion 47. In other words, the introduction unit 50 introduces the liquid L1 into the flow channel 10 at a flow rate corresponding to the flow rate of the fluid F1 flowing through the pipe portion 47. The configuration of the supply unit 40 is not limited to the configuration described above. The flow rate of the liquid L1 supplied from the containing pipe 51 to the flow channel 10 of the microfluidic device 2 may be different from the flow rate of the fluid F1 flowing out of the pipe portion 47.

The introduction unit 55 introduces the liquid L2 into the flow channel 10. The introduction unit 55 is disposed so as to introduce the liquid L2 into the injection port 12a of the inflow channel 12. The introduction unit 55 has a configuration for containing the liquid L2. In the present embodiment, the introduction unit 55 includes an containing pipe 56 in which the liquid L2 is contained. In the present embodiment, one end of the containing pipe 56 is connected to the pipe portion 48. The other end of the containing pipe 56 is disposed at the injection port 12a of the microfluidic device 2. The containing pipe 56 has a sufficient length in accordance with the volume of the liquid L2 to be contained. The containing pipe 56 is configured in a loop shape in order to save space. For example, the containing pipe 56 is a second containing pipe.

The fluid F1 that has flowed out of the pipe portion 48 flows into the containing pipe 56. As a result, the liquid L2 contained in the containing pipe 56 is pushed out by the fluid F1 that has flowed into the containing pipe 56. Specifically, the liquid L2 contained in the containing pipe 56 moves to the side opposite to the pipe portion 48 in accordance with the volume of the fluid F1 that has flowed into the containing pipe 56. Accordingly, the flow rate of the liquid L2 supplied from the containing pipe 56 to the flow channel 10 of the microfluidic device 2 is the flow rate of the fluid F1 flowing out of the pipe portion 48. In other words, the introduction unit 55 introduces the liquid L2 into the flow channel 10 at a flow rate corresponding to the flow rate of the fluid F1 flowing through the pipe portion 48. The configuration of the supply unit 40 is not limited to the configuration described above. The flow rate of the liquid L2 supplied from the containing pipe 56 to the flow channel 10 of the microfluidic device 2 may be different from the flow rate of the fluid F1 flowing out of the pipe portion 48.

The stopping portion 60 stops the flow of the fluid F1 in the pipe portion 47. The stopping portion 65 stops the flow of the fluid F1 in the pipe portion 48. In the present embodiment, the stopping portions 60 and 65 include valves 61 and 66 opening and closing the flow channels, respectively. The valve 61 opens and closes the flow channel connecting the pipe portion 47 and the introduction unit 50.

The valve 61 is provided at the connection part between the pipe portion 47 and one end of the containing pipe 51. The valve 66 opens and closes the flow channel connecting the pipe portion 48 and the introduction unit 55. The valve 66 is provided at the connection part between the pipe portion 48 and one end of the containing pipe 56. The valve 61 may open and close the flow channel connecting the introduction unit 50 and the microfluidic device 2. The valve 66 may open and close the flow channel connecting the introduction unit 55 and the microfluidic device 2.

The valves 61 and 66 may be, for example, MEMS technology-based pneumatic valves provided adjacent to the flow channel through which the fluid F1, the liquid L1, or the liquid L2 flows. In this case, the flow channel through which the fluid F1, the liquid L1, or the liquid L2 flows is pressed and the flow channel is closed as a result of an increase in air pressure in the pneumatic valve.

The pump unit 71 has a discharge port 71a for discharging the fluid F2. The pump unit 71 is, for example, a syringe pump containing the fluid F2 discharged from the discharge port 71a. The pump unit 71 may manually discharge the fluid F2 from the discharge port 71a. The pump unit 71 discharges the fluid F2 from the discharge port 71a at a constant pressure. The fluid F2 is, for example, a second fluid.

The fluid F2 discharged from the discharge port 71a by the pump unit 71 is, for example, an incompressible fluid. Examples of the incompressible fluid include a liquid. Examples of the liquid include a buffer solution. The buffer solution may be, for example, PBS.

The branch pipe 75 has a connecting portion 76 and a plurality of pipe portions 77 and 78. In the present embodiment, the branch pipe 75 has two pipe portions 77 and 78. The connecting portion 76 is connected to the discharge port 71a. The fluid F2 discharged from the discharge port 71a flows into the branch pipe 75 from the connecting portion 76. In the present embodiment, the syringe pump and the connecting portion 76 of the branch pipe 75 are connected by a silicone tube. For example, in the present embodiment, the pipe portion 47 is a first pipe portion, the pipe portion 48 is a second pipe portion, the pipe portion 77 is a third pipe portion, and the pipe portion 78 is a fourth pipe portion.

The pipe portions 77 and 78 branch off from the connecting portion 76. Accordingly, the fluid F2 that has flowed in from the connecting portion 76 flows into at least one of the pipe portions 77 and 78. The flow rate of the fluid F2 flowing into the connecting portion 76 after the branch pipe 75 is filled with the fluid F2 is the total flow rate of the fluid F2 flowing out of the pipe portions 77 and 78. Although the branch pipe 75 branches off from the connecting portion 76 into the two pipe portions 77 and 78 in the present embodiment, it may branch into three or more pipe portions 77 and 78.

The introduction unit 80 introduces the liquid L3 into the flow channel 20. The introduction unit 80 is disposed so as to introduce the liquid L3 into the injection port 21a of the inflow channel 21. The introduction unit 80 has a configuration for containing the liquid L3. In the present embodiment, the introduction unit 80 includes an containing pipe 81 in which the liquid L3 is contained. In the present embodiment, one end of the containing pipe 81 is connected to the pipe portion 77. The other end of the containing pipe 81 is disposed at the injection port 21a of the microfluidic device 2. The containing pipe 81 has a sufficient length in accordance with the volume of the liquid L3 to be contained. The containing pipe 81 is configured in a loop shape in order to save space. For example, the containing pipe 81 is a third containing pipe.

The fluid F2 that has flowed out of the pipe portion 77 flows into the containing pipe 81. As a result, the liquid L3 contained in the containing pipe 81 is pushed out by the fluid F2 that has flowed into the containing pipe 81. Specifically, the liquid L3 contained in the containing pipe 81 moves to the side opposite to the pipe portion 77 in accordance with the volume of the fluid F2 that has flowed into the containing pipe 81. Accordingly, the flow rate of the liquid L3 supplied from the containing pipe 81 to the flow channel 20 of the microfluidic device 2 is the flow rate of the fluid F2 flowing out of the pipe portion 77. In other words, the introduction unit 80 introduces the liquid L3 into the flow channel 20 at a flow rate corresponding to the flow rate of the fluid F2 flowing through the pipe portion 77. The configuration of the supply unit 70 is not limited to the configuration described above. The flow rate of the liquid L3 supplied from the containing pipe 81 to the flow channel 20 of the microfluidic device 2 may be different from the flow rate of the fluid F2 flowing out of the pipe portion 77.

The introduction unit 85 introduces the liquid L4 into the flow channel 20. The introduction unit 85 is disposed so as to introduce the liquid L4 into the injection port 22a of the inflow channel 22. The introduction unit 85 has a configuration for containing the liquid L4. In the present embodiment, the introduction unit 85 includes an containing pipe 86 in which the liquid L4 is contained. In the present embodiment, one end of the containing pipe 86 is connected to the pipe portion 78. The other end of the containing pipe 86 is disposed at the injection port 22a of the microfluidic device 2. The containing pipe 86 has a sufficient length in accordance with the volume of the liquid L4 to be contained. The containing pipe 86 is configured in a loop shape in order to save space. In the present embodiment, the introduction unit 85 contains the liquid L4 in the containing pipe 86 and the volume of the contained liquid L4 exceeds the volume of the flow channel 20 from the connection position between the inflow channel 21 and the flow channel 20 to the connection position between the flow channel 20 and the communication hole 33 in the extension direction D1. For example, the containing pipe 86 is a fourth containing pipe.

The fluid F2 that has flowed out of the pipe portion 78 flows into the containing pipe 86. As a result, the liquid L4 contained in the containing pipe 86 is pushed out by the fluid F2 that has flowed into the containing pipe 86. Specifically, the liquid L4 contained in the containing pipe 86 moves to the side opposite to the pipe portion 78 in accordance with the volume of the fluid F2 that has flowed into the containing pipe 86. Accordingly, the flow rate of the liquid L4 supplied from the containing pipe 86 to the flow channel 20 of the microfluidic device 2 is the flow rate of the fluid F2 flowing out of the pipe portion 78. In other words, the introduction unit 85 introduces the liquid L4 into the flow channel 20 at a flow rate corresponding to the flow rate of the fluid F2 flowing through the pipe portion 78. The configuration of the supply unit 70 is not limited to the configuration described above. The flow rate of the liquid L4 supplied from the containing pipe 86 to the flow channel 20 of the microfluidic device 2 may be different from the flow rate of the fluid F2 flowing out of the pipe portion 78.

The stopping portion 90 stops the flow of the fluid F2 in the pipe portion 77. The stopping portion 95 stops the flow of the fluid F2 in the pipe portion 78. In the present embodiment, the stopping portions 90 and 95 include valves 91 and 96 opening and closing the flow channels, respectively. The valve 91 opens and closes the flow channel connecting the pipe portion 77 and the introduction unit 80. The valve 91 is provided at the connection part between the pipe portion 77 and one end of the containing pipe 81. The valve 96 opens and closes the flow channel connecting the pipe portion 78 and the introduction unit 85. The valve 96 is provided at the connection part between the pipe portion 78 and one end of the containing pipe 86 and. The valve 91 may open and close the flow channel connecting the introduction unit 80 and the microfluidic device 2. The valve 96 may open and close the flow channel connecting the introduction unit 85 and the microfluidic device 2.

The valves 91 and 96 may be, for example, MEMS technology-based pneumatic valves provided adjacent to the flow channel through which the fluid F2, the liquid L3, or the liquid L4 flows. In this case, the flow channel through which the fluid F2, the liquid L3, or the liquid L4 flows is pressed and the flow channel is closed as a result of an increase in air pressure in the pneumatic valve.

Figure 3:
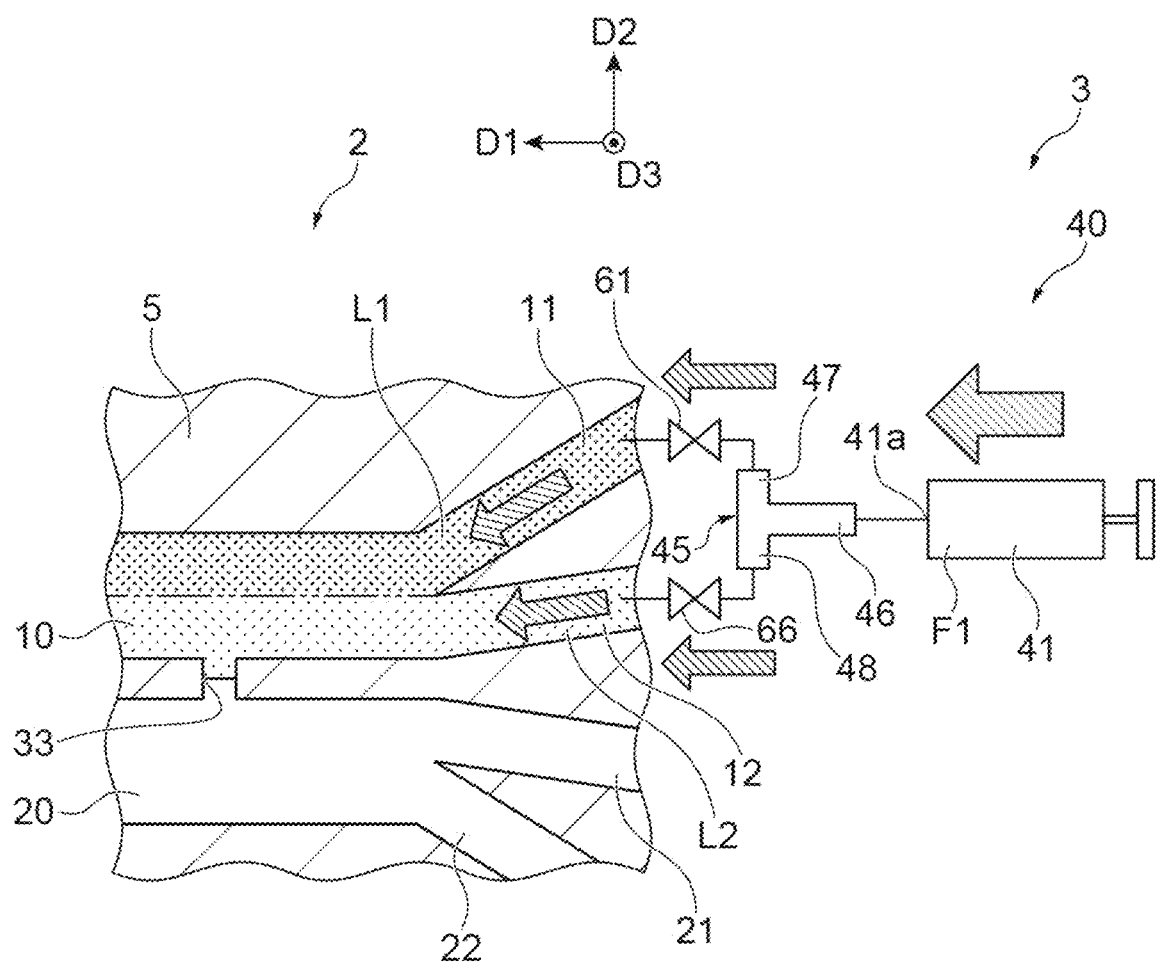
FIG. 3 is a diagram for describing the operation of the microdevice system.
Figure 4:
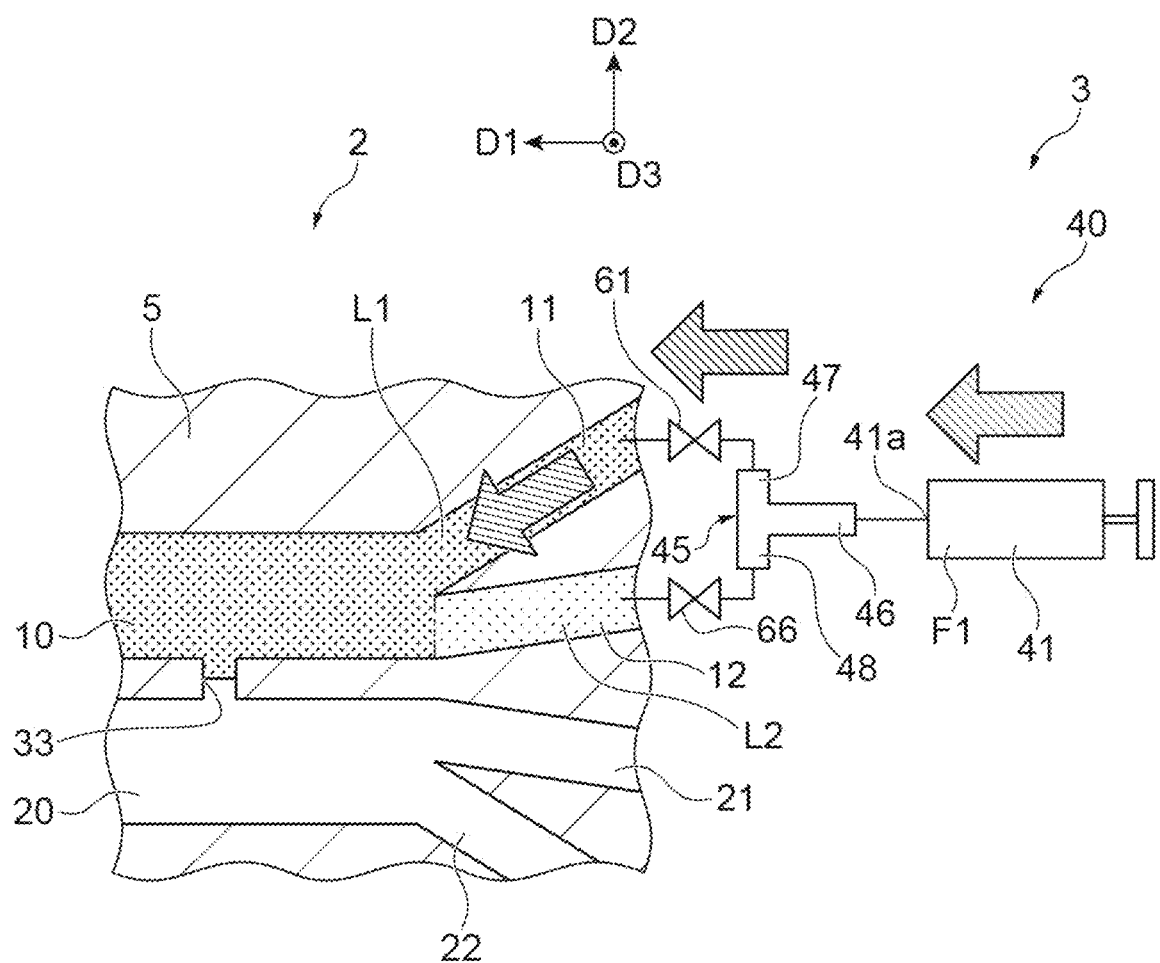
FIG. 4 is a diagram for describing the operation of the microdevice system.

Next, the liquid supply operation in the microdevice system 1 will be described in detail with reference to FIGS. 1, 3, and 4. Although only a part of the microfluidic device 2 and the supply unit 40 are illustrated in FIGS. 3 and 4, a case where the liquid is supplied to the flow channel 20 by the supply unit 70 will also be described along with a case where the liquid is supplied to the flow channel 10 by the supply unit 40. FIG. 3 illustrates a state where both the valve 61 and the valve 66 of the supply unit 40 are open. FIG. 4 illustrates a state where the valve 66 of the supply unit 40 is closed. In FIGS. 3 and 4, arrows indicate the flow rates of the fluid F1 and the liquids L1 and L2. The wider the arrow, the higher the flow rate. In FIGS. 3 and 4, two-dot chain lines indicate the boundary between the liquid L1 and the liquid L2. The liquid L1 and the liquid L2 are mixed at this boundary.

As illustrated in FIG. 3, in a state where both the valve 61 and the valve 66 of the supply unit 40 are open, the fluid F1 introduced from the pump unit 41 into the branch pipe 45 flows out of both the pipe portion 47 and the pipe portion 48. In this case, the liquid L1 is introduced from the introduction unit 50 into the inflow channel 11 and the liquid L2 is introduced from the introduction unit 55 into the inflow channel 12. The liquid L1 that has flowed through the inflow channel 11 and the liquid L2 that has flowed through the inflow channel 12 merge at the flow channel 10. The merged liquid L1 and liquid L2 flow through the flow channel 10 in parallel to each other and in the extension direction D1. In other words, a layer through which the liquid L1 flows and a layer through which the liquid L2 flows are formed in the flow channel 10. When viewed in the direction D3, the liquid L2 flows on the flow channel 20 side. In other words, the flow of the liquid L2 is closer to the flow channel 20 than the flow of the liquid L1 in the direction D2. Accordingly, only the liquid L2 is supplied to the flow channel 10 side of the communication hole 33.

In a state where both the valve 91 and the valve 96 of the supply unit 70 are open, the fluid F2 introduced from the pump unit 71 into the branch pipe 75 flows out of both the pipe portion 77 and the pipe portion 78. In this case, the liquid L3 is introduced from the introduction unit 80 into the inflow channel 21 and the liquid L4 is introduced from the introduction unit 85 into the inflow channel 22. The liquid L3 that has flowed through the inflow channel 21 and the liquid L4 that has flowed through the inflow channel 22 merge at the flow channel 20. The merged liquid L3 and liquid L4 flow through the flow channel 20 in parallel to each other and in the extension direction D1 as in the case of the liquids L1 and L2. In other words, a layer through which the liquid L3 flows and a layer through which the liquid L4 flows are formed in the flow channel 20. When viewed in the direction D3, the liquid L3 flows on the flow channel 10 side. In other words, the flow of the liquid L3 is closer to the flow channel 10 than the flow of the liquid L4 in the direction D2. Accordingly, only the liquid L3 is supplied to the flow channel 20 side of the communication hole 33.

As illustrated in FIG. 4, in a state where the valve 61 is open and the valve 66 is closed, the fluid F1 introduced from the pump unit 41 into the branch pipe 45 flows out of the pipe portion 47 and does not flow out of the pipe portion 48. Accordingly, the liquid L2 is not introduced from the introduction unit 55 into the inflow channel 12 although the liquid L1 is introduced from the introduction unit 50 into the inflow channel 11. Accordingly, the flow of the liquid L2 in the inflow channel 12 stops and only the liquid L1 flows through the flow channel 10 in the extension direction D1. At this time, the liquid L1 flushes the liquid L2 remaining in the flow channel 10. As a result, only the liquid L1 is supplied to the flow channel 10 side of the communication hole 33.

In a state where the valve 61 is open and the valve 66 is closed, the flow rate of the fluid F1 flowing through the pipe portion 47 increases as the flow rate of the fluid F1 flowing through the pipe portion 48 decreases. In the present embodiment, the entire fluid F1 newly introduced into the branch pipe 45 from the pump unit 41 flows out of the pipe portion 47. As a result, the flow rate of the fluid F1 in the pipe portion 47 increases from the state where both the valve 61 and the valve 66 are open. Accordingly, the flow rate of the liquid L1 introduced from the introduction unit 50 into the inflow channel 11 also increases from the state where both the valve 61 and the valve 66 are open. Accordingly, a change in the flow rate of the liquid flowing in the flow channel 10 is suppressed and a pressure change in the flow channel 10 is suppressed even in the event of a switch from the state where both the valve 61 and the valve 66 are open to the state where the valve 66 is closed.

In a state where the valve 96 is open and the valve 91 is closed, the fluid F2 introduced from the pump unit 71 into the branch pipe 75 flows out of the pipe portion 78 and does not flow out of the pipe portion 77. Accordingly, the liquid L3 is not introduced from the introduction unit 80 into the inflow channel 21 although the liquid L4 is introduced from the introduction unit 85 into the inflow channel 22. Accordingly, the flow of the liquid L3 in the inflow channel 21 stops and only the liquid L4 flows through the flow channel 20 in the extension direction D1. At this time, the liquid L4 flushes the liquid L3 remaining in the flow channel 20. As a result, only the liquid L4 is supplied to the flow channel 20 side of the communication hole 33.

In a state where the valve 96 is open and the valve 91 is closed, the flow rate of the fluid F2 flowing through the pipe portion 78 increases as the flow rate of the fluid F2 flowing through the pipe portion 77 decreases. In the present embodiment, the entire fluid F2 newly introduced into the branch pipe 75 from the pump unit 71 flows out of the pipe portion 78. As a result, the flow rate of the fluid F2 in the pipe portion 78 increases from the state where both the valve 91 and the valve 96 are open. Accordingly, the flow rate of the liquid L4 introduced from the introduction unit 85 into the inflow channel 22 also increases from the state where both the valve 91 and the valve 96 are open. Accordingly, a pressure change in the flow channel 20 is suppressed even in the event of a switch from the state where both the valve 91 and the valve 96 are open to the state where the valve 91 is closed.

Next, a method for using the microdevice system in the present embodiment will be described. In the present embodiment, a case where the microdevice system 1 is used for observing a cell reaction to a target substance will be described. In the present embodiment, the liquids L1 and L3 are, for example, buffer solutions. This buffer solution may be, for example, HBS buffer (140 mM NaCl, 5 mM KCl, 2 mM $CaCl_2$, 1 mM $MgCl_2$, 10 mM glucose, 0.2% bovine serum albumin (BSA), and 10 mM HEPES (pH 7.4)). The liquid L2 is a suspension containing a plurality of cells (hereinafter, referred to as "cell suspension"). The liquid L4 is a sample containing a target substance to be brought into contact with a cell (hereinafter, simply referred to as "sample"). The liquid L1 does not contain cells. The liquid L3 does not contain the target substance. Fluorescent dyes may be added to the liquids L1, L2, L3, and L4 so that the respective flows are confirmed.

The diameter of the communication hole 33 of the microfluidic device 2 in the present embodiment is smaller than the diameter of the cell. For example, the diameter of the communication hole 33 is less than 75% of the cell diameter. For example, the diameter of the communication hole 33 is 1 to 15 μm. In the present embodiment, the diameter of the communication hole 33 is 3 μm.

The cell used in the present embodiment has a fluorescent indicator.

The target substance is not particularly limited and may be a stimulant such as ATP and histamine.

The fluorescent indicator is not particularly limited insofar as it is a substance that fluoresces as a result of stimulation by the target substance. The fluorescent indicator may be, for example, a fluorescent protein or a fluorescent dye. Preferably, the fluorescent indicator is a genetically encoded fluorescent protein. When the stimulation by the target substance results in, for example, a change in intracellular ion concentration, the fluorescent indicator may be a fluorescent protein or a fluorescent dye sensitive to the ion. Examples of the fluorescent protein include GCaMP3, GCaMP6s, and GCaMP7 proteins as calcium-sensitive fluorescent proteins. Examples of the fluorescent dye include calcium-sensitive fluorescent dyes such as Fluo 3-AM, Rhod 2-AM, Calbryte (trademark) 520, Fluo 4-AM, Fura 2-AM, Indo 1-AM, Calbryte 590, and Calbryte 630.

The cells are, for example, human cervical epithelial cancer cells HeLa.

Figure 5:
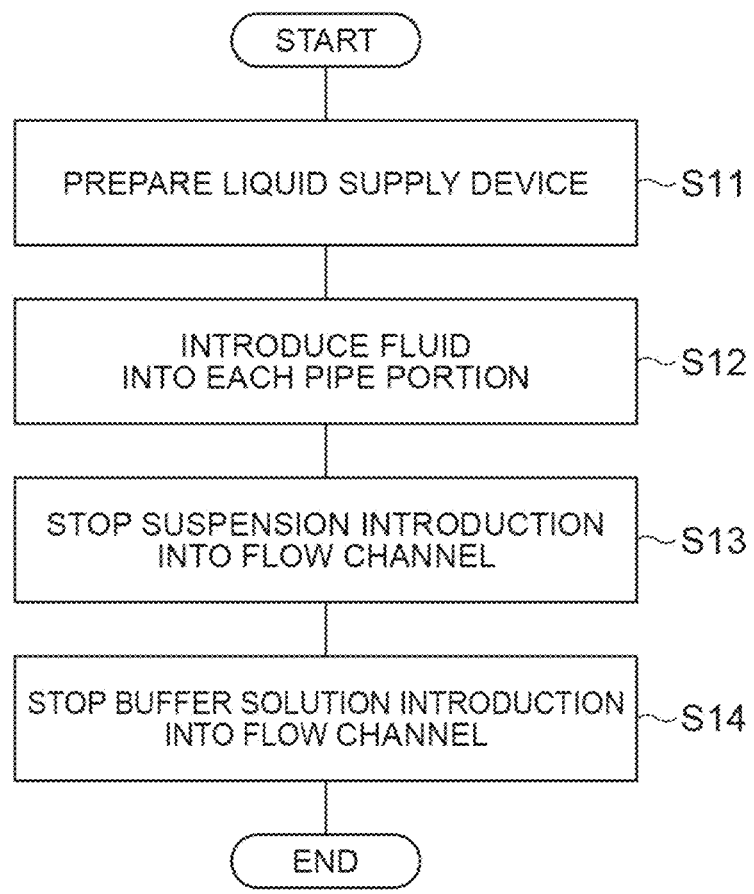
FIG. 5 is a flowchart illustrating a method for supplying a liquid to the microfluidic device.
Figure 6:
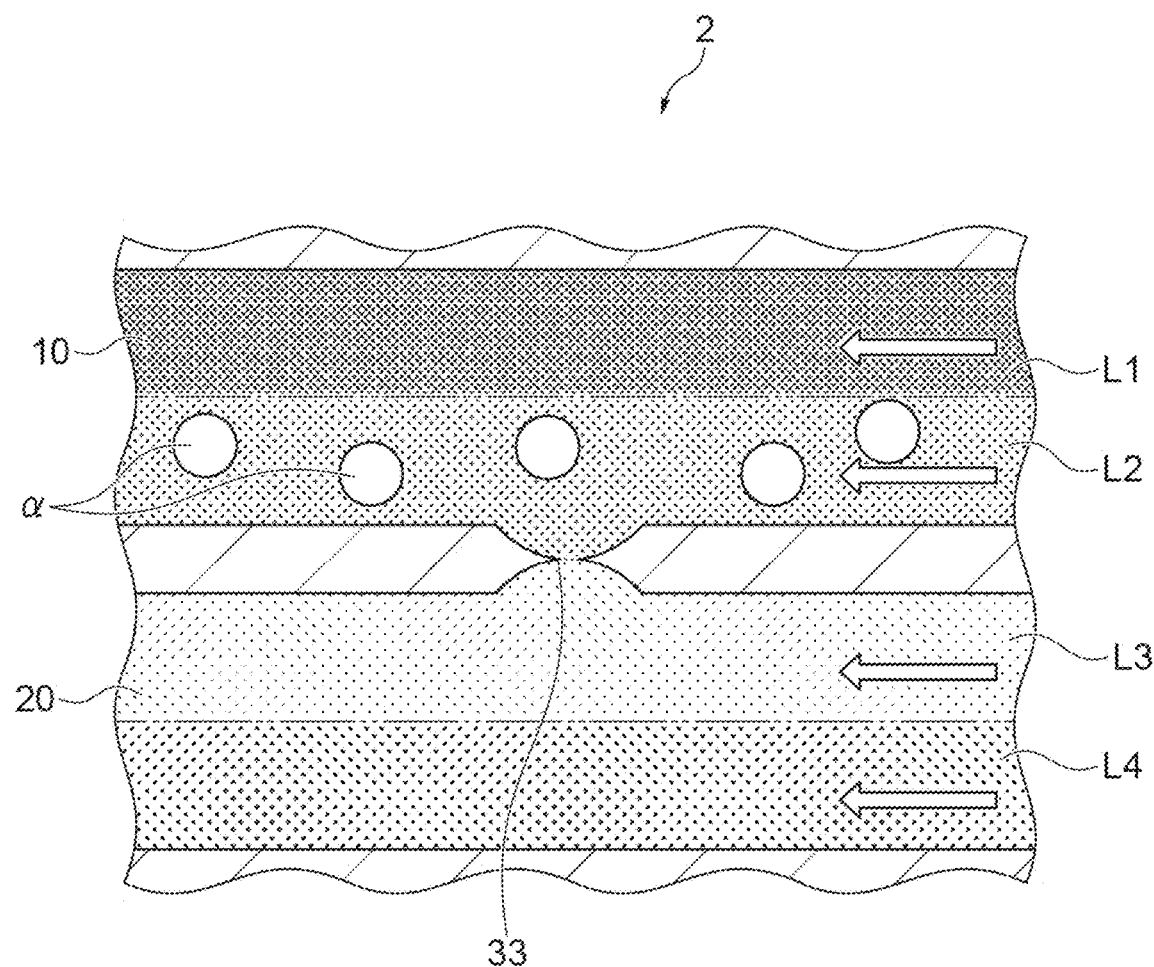
FIG. 6 is a diagram for describing the method for supplying the liquid to the microfluidic device. p
Figure 7:
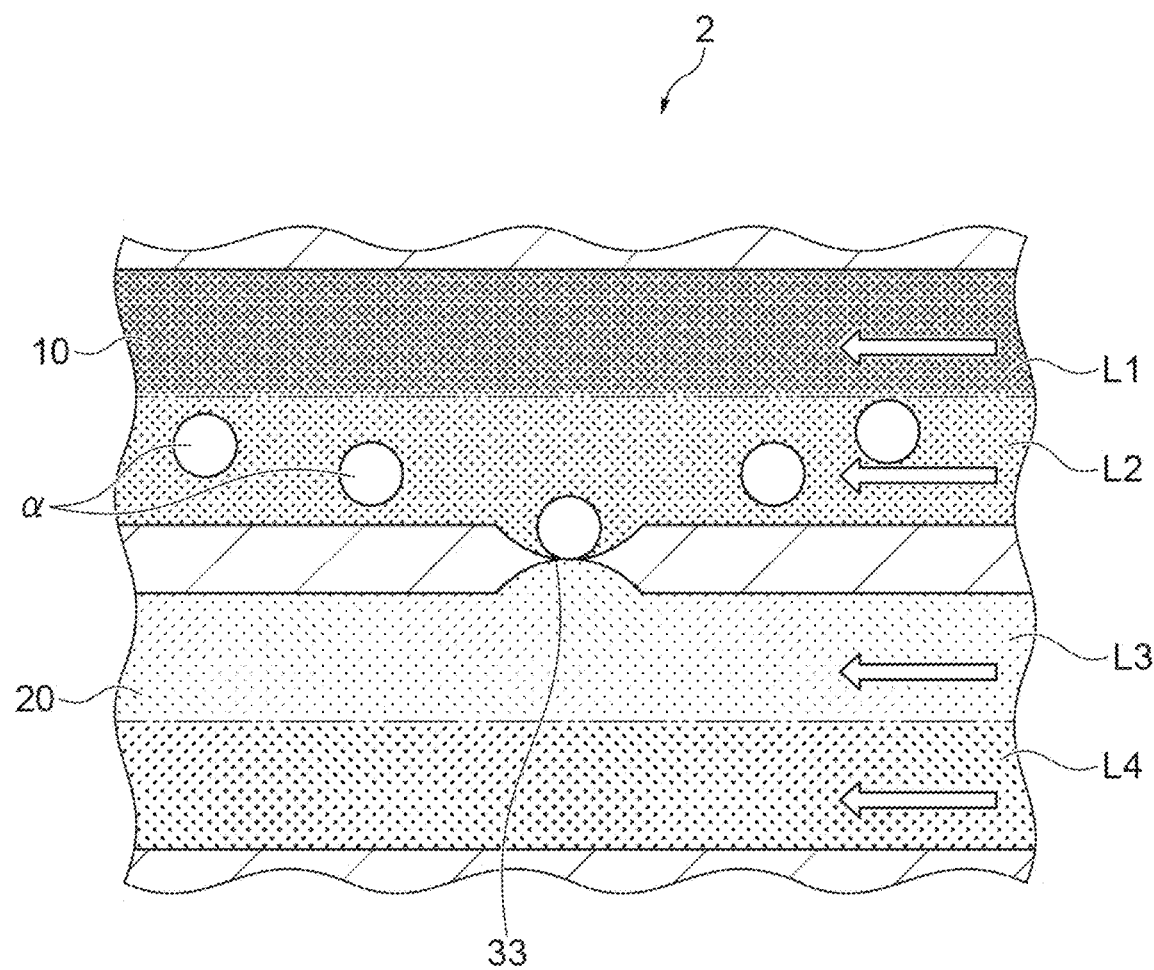
FIG. 7 is a diagram for describing the method for supplying the liquid to the microfluidic device.
Figure 8:
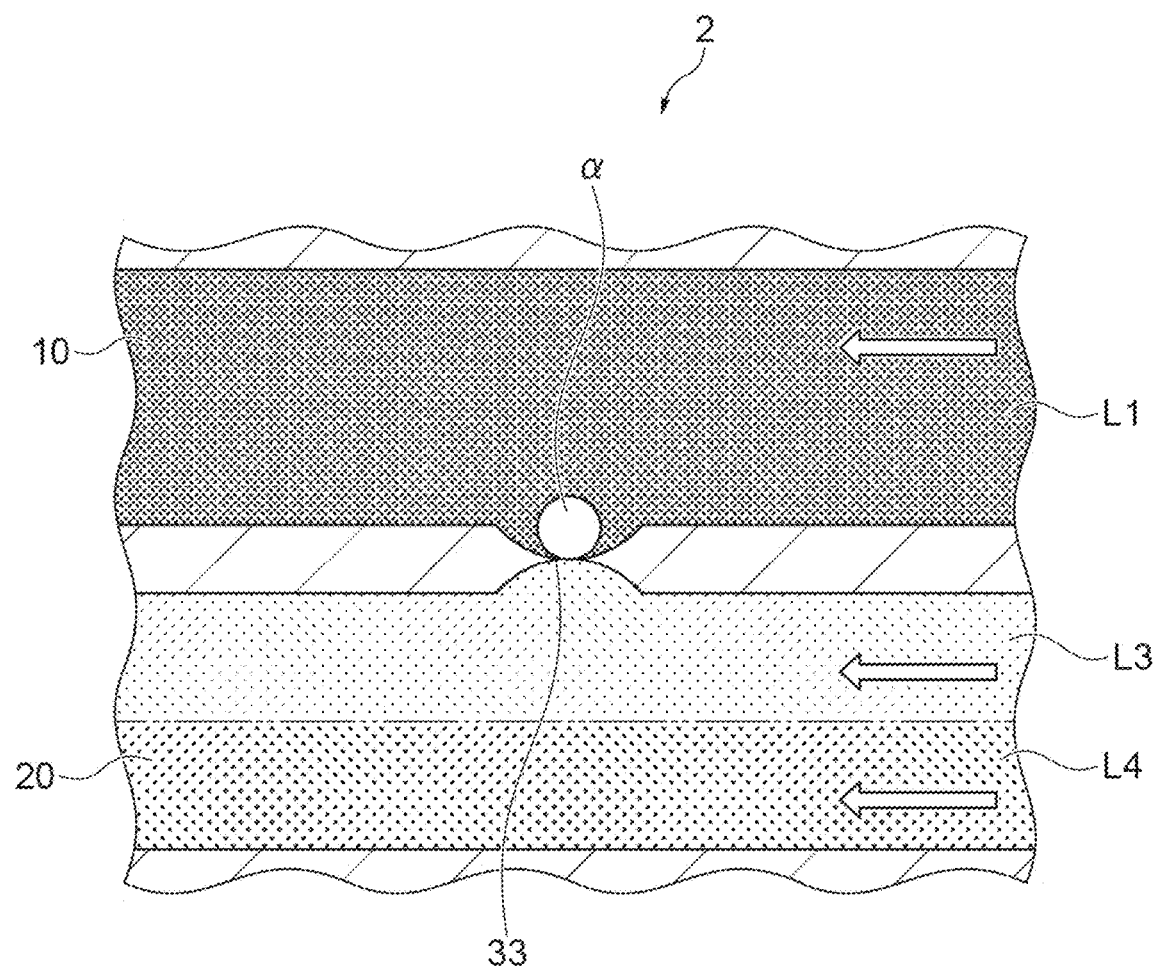
FIG. 8 is a diagram for describing the method for supplying the liquid to the microfluidic device.

Next, a method for supplying a liquid to the microfluidic device 2 in the present embodiment will be described with reference to FIGS. 5 to 9. FIG. 5 is a flowchart illustrating the method for supplying the liquid to the microfluidic device 2 in the present embodiment. FIGS. 6 to 9 are diagrams for describing each step of the method for supplying the liquid to the microfluidic device 2. In FIGS. 6 to 9, arrows indicate the flow direction of the liquid. In FIGS. 6 to 8, two-dot chain lines indicate the boundary between different liquids. The different liquids are mixed at this boundary.

First, as illustrated in FIG. 5, the liquid supply device 3 for liquid supply to the microfluidic device 2 is prepared (process S11). Specifically, the introduction unit 50 is disposed so as to introduce the buffer solution as the liquid L1 into the injection port 11a of the inflow channel 11. The introduction unit 55 is disposed so as to introduce the cell suspension as the liquid L2 into the injection port 12a of the inflow channel 12. The introduction unit 80 is disposed so as to introduce the buffer solution as the liquid L3 into the injection port 21a of the inflow channel 21. The introduction unit 85 is disposed so as to introduce the sample as the liquid L4 into the injection port 22a of the inflow channel 22.

Subsequently, as illustrated in FIG. 5, the fluids F1 and F2 are introduced into the pipe portions 47, 48, 77, and 78 by the pump units 41 and 71 (process S12). Specifically, the fluid F1 is discharged at a constant flow rate from the discharge port 41a of the pump unit 41 of the supply unit 40 and the fluid F1 is caused to flow into the pipe portions 47 and 48. The fluid F2 is discharged at a constant flow rate from the discharge port 71a of the pump unit 71 of the supply unit 70 and the fluid F2 is caused to flow into the pipe portions 77 and 78. At this time, the valves 61, 66, 91, and 96 are open without exception. As a result, as illustrated in FIG. 6, the liquids L1 and L2 are introduced into the flow channel 10 and the liquids L3 and L4 are introduced into the flow channel 20 by the liquid supply device 3. The buffer solution and the cell suspension flow in parallel through the flow channel 10 such that the cell suspension flows closer to the flow channel 20 than the buffer solution. The buffer solution and the sample flow in parallel through the flow channel 20 such that the buffer solution flows closer to the flow channel 10 than the sample. In other words, a layer through which the buffer solution flows and a layer through which the cell suspension flows are formed in the flow channel 10. A layer through which the buffer solution flows and a layer through which the sample flows are formed in the flow channel 20.

In the present embodiment, the fluids F1 and F2 are discharged from the pump unit 41 of the supply unit 40 and the pump unit 71 of the supply unit 70 such that the pressure in the flow channel 10 becomes higher than the pressure in the flow channel 20. Accordingly, a pressure difference occurs in the communication hole 33. As a result of this pressure difference, a cell α in the liquid L2 is captured at the communication hole 33 on the flow channel 10 side as illustrated in FIG. 7. It should be noted that "pressure" in the flow channel means a static pressure. Accordingly, "pressure difference" is the difference in static pressure between the flow channels.

In the present embodiment, the pressure in the flow channel 10 becomes higher than the pressure in the flow channel 20 owing to the difference between the total flow rate of the liquids L1 and L2 flowing through the flow channel 10 and the total flow rate of the liquids L3 and L4 flowing through the flow channel 20. However, the pressure in the flow channel 10 may become higher than the pressure in the flow channel 20 owing to the difference in shape between the flow channel 10 and the flow channel 20 instead of the difference between the flow rate flowing through the flow channel 10 and the flow rate of the flow channel 20. In the process S12, the total flow rate of the liquids L1 and L2 flowing through the flow channel 10 is 60 µL/h. The total flow rate of the liquids L3 and L4 flowing through the flow channel 20 is 40 µL/h.

Subsequently, as illustrated in FIG. 5, the cell suspension introduction into the flow channel 10 is stopped (process S13). Specifically, the valve 66 is closed and the flow of the fluid F1 in the pipe portion 48 is stopped while the fluid F1 is caused to flow into the pipe portion 47. The fluid F2 flows in the pipe portions 77 and 78. As a result, as illustrated in FIG. 8, only the buffer solution as the liquid L1 flows through the flow channel 10 and the cell α not captured at the communication hole 33 is washed away. As in the case of the process S12, the buffer solution and the sample as the liquids L3 and L4 flow in parallel in the flow channel 20.

The flow rate of the fluid F1 discharged by the pump unit 41 of the supply unit 40 and the flow rate of the fluid F2 discharged by the pump unit 71 of the supply unit 70 in the process S12 are maintained in the process S13. Since the valve 66 is closed and the flow of the fluid F1 in the pipe portion 48 is stopped, the flow rate of the fluid F1 in the pipe portion 47 increases by the flow rate of the fluid F1 flowing in the pipe portion 48 in the process S12. As a result, the flow rate of the buffer solution flowing through the flow channel 10 increases by the flow rate of the cell suspension flowing through the flow channel 10 in the process S12. Accordingly, a pressure change in the flow channel 10 is suppressed regardless of the switch from the process S12 to the process S13.

Figure 9:
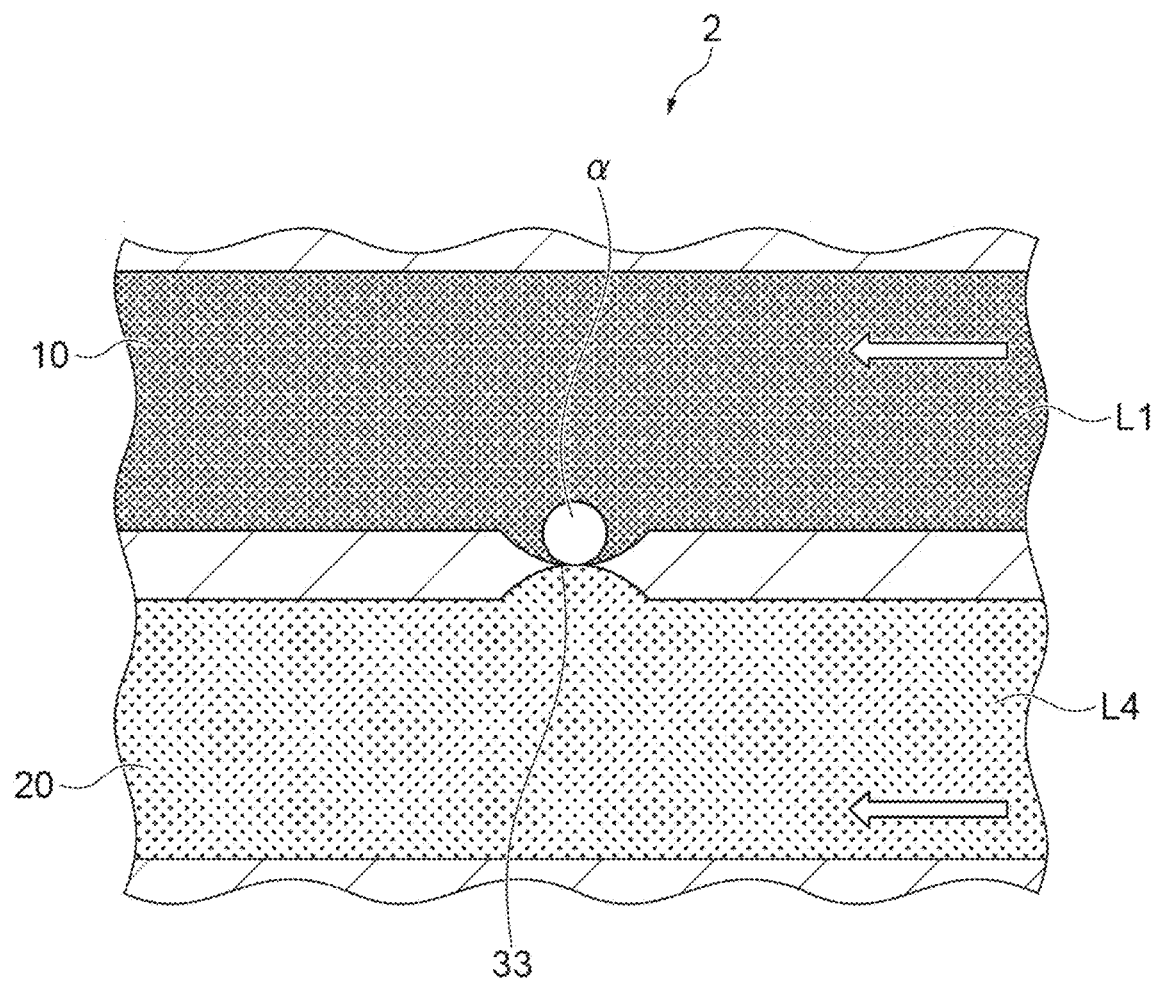
FIG. 9 is a diagram for describing the method for supplying the liquid to the microfluidic device.

Subsequently, as illustrated in FIG. 5, the buffer solution introduction into the flow channel 20 is stopped (process S14). Specifically, the valve 91 is closed and the flow of the fluid F2 in the pipe portion 77 is stopped while the fluid F2 is caused to flow into the pipe portion 78. The fluid F1 flows in the pipe portion 47. The flow of the fluid F1 in the pipe portion 48 is stopped. As a result, as illustrated in FIG. 9, only the sample as the liquid L4 flows into the flow channel 20 and the sample containing the target substance also flows into the communication hole 33 side of the flow channel 20. Accordingly, through the communication hole 33, the target substance comes into contact with the cell α captured by the communication hole 33. As a result, the reaction of the cell α to the target substance is initiated.

The flow rate of the fluid F1 discharged by the pump unit 41 of the supply unit 40 and the flow rate of the fluid F2 discharged by the pump unit 71 of the supply unit 70 in the process S12 and the process S13 are maintained in the process S14. Since the valve 91 is closed and the flow of the fluid F2 in the pipe portion 77 is stopped, the flow rate of the fluid F2 in the pipe portion 78 increases by the flow rate of the fluid F2 flowing in the pipe portion 77 in the process S12 and the process S13. As a result, the flow rate of the sample flowing through the flow channel 20 increases by the flow rate of the buffer solution flowing through the flow channel 20 in the process S12 and the process S13. Accordingly, a pressure change in the flow channel 20 is suppressed regardless of the switch from the process S13 to the process S14.

Next, a method for using the microdevice system according to a modification example of the present embodiment will be described. Described in this modification example is a case where the microdevice system 1 is used for lipid bilayer membrane formation. The microdevice system in this modification example is generally similar or identical to the embodiment described above. In the microdevice system of this modification example, the diameter of the communication hole 33 of the microfluidic device 2 and the types of the liquids L1, L2, L3, and L4 are different from those of the embodiment described above. Hereinafter, the differences between the above-described embodiment and the modification example will be mainly described.

The diameter of the communication hole 33 of the microfluidic device 2 in this modification example is larger than the diameter of the communication hole 33 in the embodiment described above. For example, the upper limit of the diameter of the communication hole 33 in this modification example is equal to or less than the depth of the flow channels 10 and 20. In other words, the diameter of the communication hole 33 may be 100 µm insofar as the depth of the flow channels 10 and 20 is 100 µm. In the microfluidic device 2 of this modification example, the diameter of the communication hole 33 may be, for example, 1 to 30 µm. In this modification example, the diameter of the communication hole 33 is 10 µm. The liquids L2 and L3 are lipid-dissolved oily solutions (hereinafter, simply referred to as "oily solutions"). The liquids L1 and L4 are aqueous solutions. Fluorescent dyes may be added to the liquids L1, L2, L3, and L4 so that the respective flows are confirmed.

The lipid is a component forming a lipid bilayer membrane and has a hydrophilic group (hydrophilic atomic group) and a hydrophobic group (hydrophobic atomic group). The lipid is appropriately selected depending on the lipid bilayer membrane to be formed. The lipid is, for example, phospholipid, glycolipid, cholesterol, or another compound. Examples of the phospholipid include phosphatidylcholine, phosphatidylethanolamine, phosphatidylserine, phosphatidylinositol, and sphingomyelin. Examples of the glycolipid include cerebroside and ganglioside.

Various organic solvents are appropriately selected as an oily solvent for lipid dissolution. Examples of the oily organic solvent include hexadecane and squalene.

The aqueous solution of the liquids L1 and L4 is, for example, a buffer solution. The buffer solution may be, for example, PBS. The aqueous solution of the liquids L1 and L4 contains various components that do not affect the lipid bilayer membrane formation.

Figure 10:
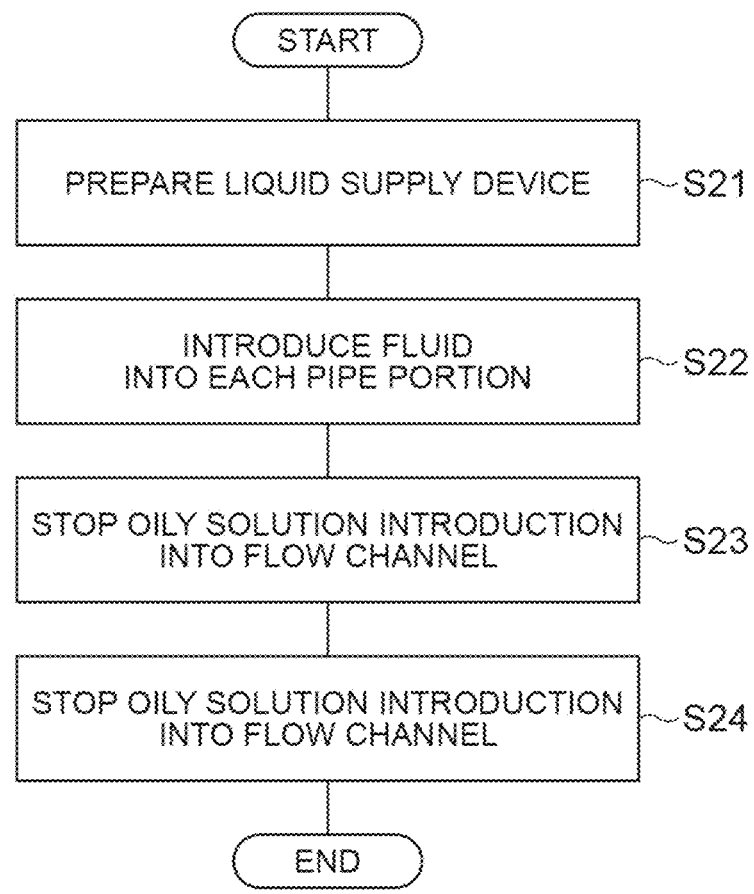
FIG. 10 is a flowchart illustrating a method for supplying a liquid to the microfluidic device in the microdevice system according to a modification example of the present embodiment.
Figure 11:
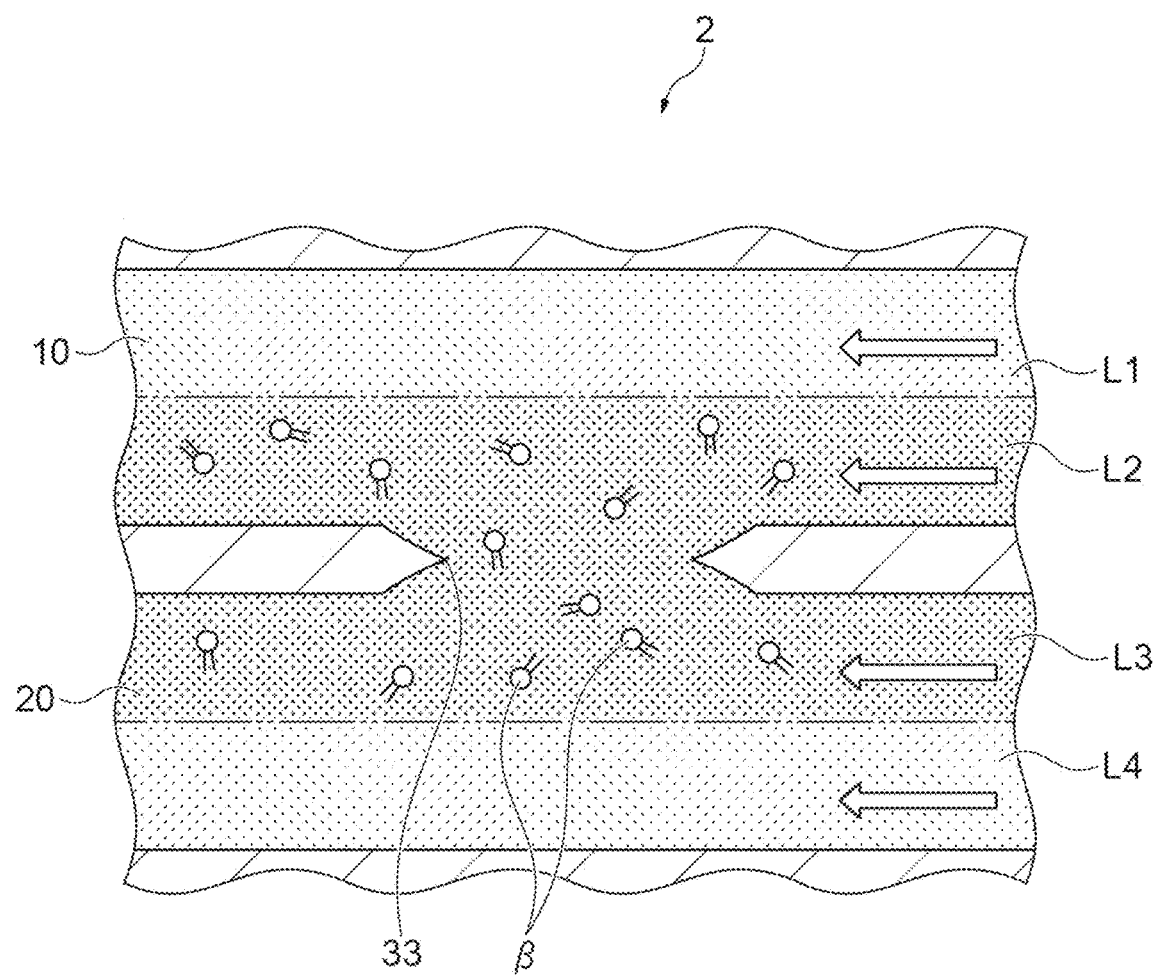
FIG. 11 is a diagram for describing the method for supplying the liquid to the microfluidic device.
Figure 12:
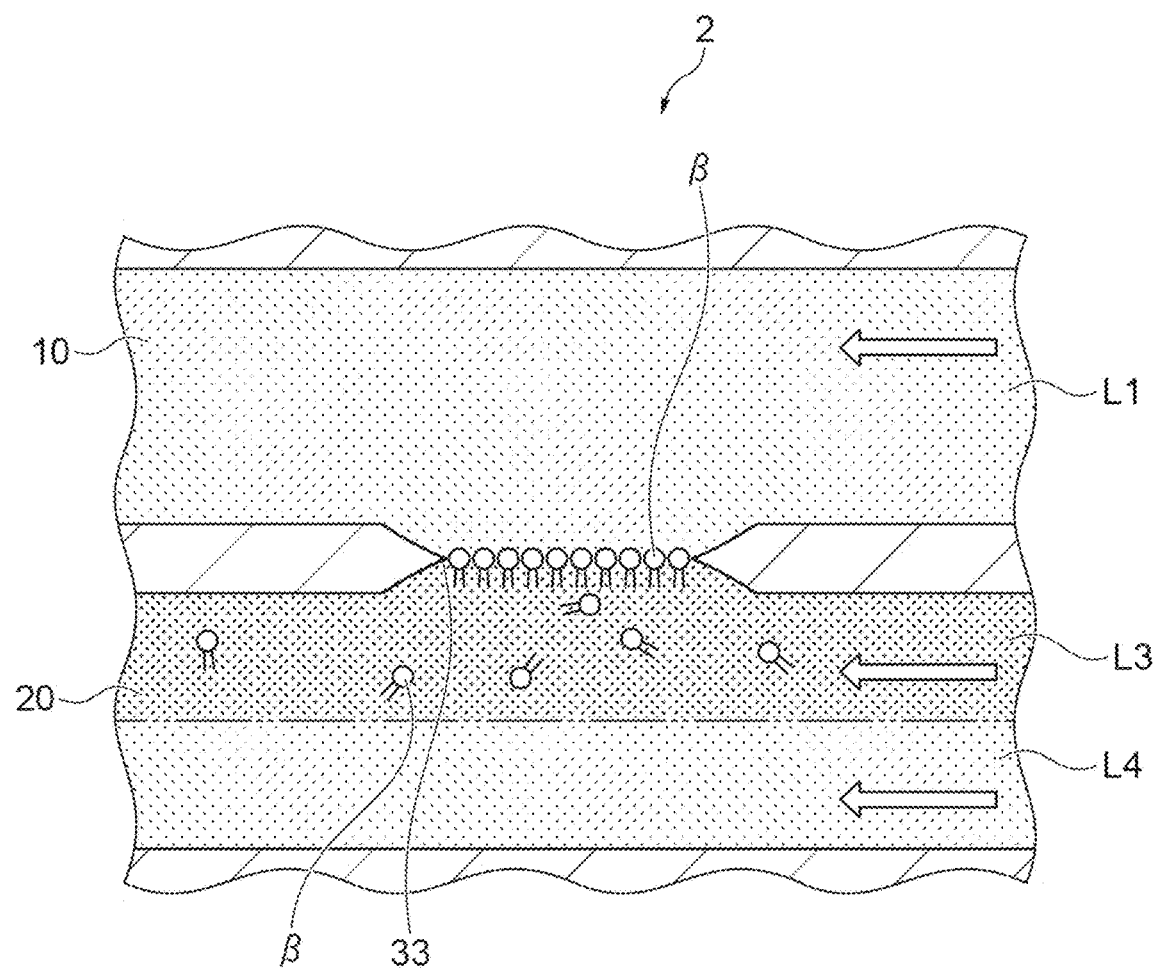
FIG. 12 is a diagram for describing the method for supplying the liquid to the microfluidic device.
Figure 13:
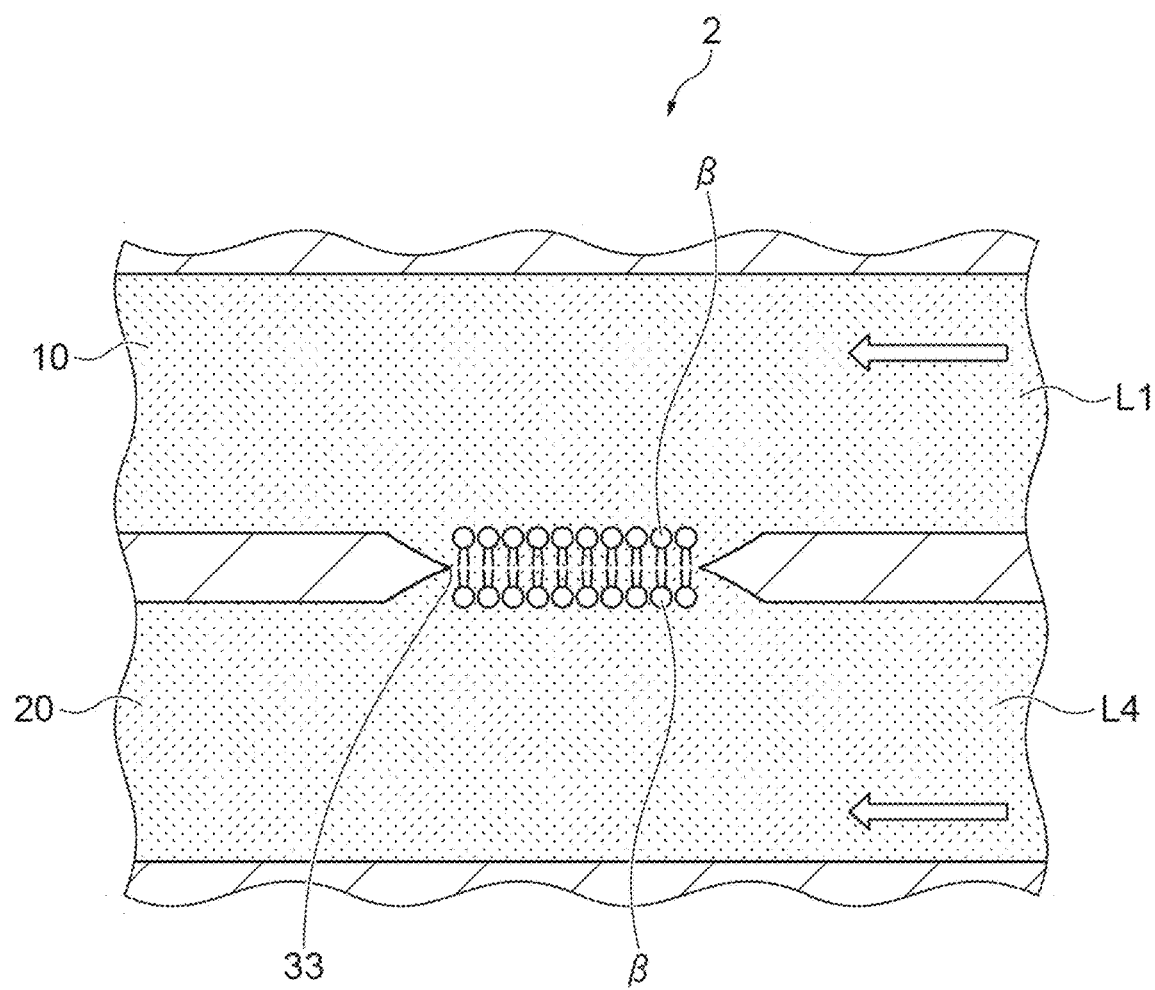
FIG. 13 is a diagram for describing the method for supplying the liquid to the microfluidic device.

Next, a method for supplying a liquid to the microfluidic device 2 in this modification example will be described with reference to FIGS. 10 to 13. FIG. 10 is a flowchart illustrating the method for supplying the liquid to the microfluidic device 2 in this modification example. FIGS. 11 to 13 are diagrams for describing each step of the method for supplying the liquid to the microfluidic device 2. In FIGS. 11 to 13, arrows indicate the flow direction of the liquid. In FIGS. 11 and 12, two-dot chain lines indicate the boundary between different liquids. The different liquids are mixed at this boundary.

First, as illustrated in FIG. 10, the liquid supply device 3 for liquid supply to the microfluidic device 2 is prepared (process S21). Specifically, the introduction unit 50 is disposed so as to introduce the aqueous solution as the liquid L1 into the injection port 11a of the inflow channel 11. The introduction unit 55 is disposed so as to introduce the oily solution as the liquid L2 into the injection port 12a of the inflow channel 12. The introduction unit 80 is disposed so as to introduce the oily solution as the liquid L3 into the injection port 21a of the inflow channel 21. The introduction unit 85 is disposed so as to introduce the aqueous solution as the liquid L4 into the injection port 22a of the inflow channel 22.

Subsequently, as illustrated in FIG. 10, the fluids F1 and F2 are introduced into the pipe portions 47, 48, 77, and 78 by the pump units 41 and 71 (process S22). Specifically, the fluid F1 is discharged at a constant flow rate from the discharge port 41*a* of the pump unit 41 of the supply unit 40 and the fluid F1 is caused to flow into the pipe portions 47 and 48. The fluid F2 is discharged at a constant flow rate from the discharge port 71*a* of the pump unit 71 of the supply unit 70 and the fluid F2 is caused to flow into the pipe portions 77 and 78. At this time, the valves 61, 66, 91, and 96 are open without exception. As a result, as illustrated in FIG. 11, the liquids L1 and L2 are introduced into the flow channel 10 and the liquids L3 and L4 are introduced into the flow channel 20 by the liquid supply device 3. The aqueous solution and the oily solution flow in parallel through the flow channel 10 such that the oily solution flows closer to the flow channel 20 than the aqueous solution. The oily solution and the aqueous solution flow in parallel through the flow channel 20 such that the oily solution flows closer to the flow channel 10 than the aqueous solution. In other words, a layer through which the aqueous solution flows and a layer through which the oily solution flows are formed in each of the flow channel 10 and the flow channel 20.

In this modification example, the fluids F1 and F2 are discharged from the pump unit 41 of the supply unit 40 and the pump unit 71 of the supply unit 70 such that the pressure in the flow channel 10 and the pressure in the flow channel 20 become equal to each other. This "equal" includes a case where a pressure difference occurs to the extent that the lipid membrane formed in the communication hole 33 is not crushed. It should be noted that "pressure" in the flow channel means a static pressure. Accordingly, "pressure difference" is the difference in static pressure between the flow channels.

In this modification example, the pressure in the flow channel 10 and the pressure in the flow channel 20 are equal to each other by the total flow rate of the liquids L1 and L2 flowing through the flow channel 10 and the total flow rate of the liquids L3 and L4 flowing through the flow channel 20 being equal to each other. However, even with the flow rate flowing through the flow channel 10 and the flow rate of the flow channel 20 different from each other, the pressure in the flow channel 10 may be equal to the pressure in the flow channel 20 by the flow channel 10 and the flow channel 20 having different shapes. In the process S22, the total flow rate of the liquids L1 and L2 flowing through the flow channel 10 is 10 µL/h. The total flow rate of the liquids L3 and L4 flowing through the flow channel 20 is 10 µL/h.

Subsequently, as illustrated in FIG. 10, the oil and fat solution introduction into the flow channel 10 is stopped (process S23). Specifically, the valve 66 is closed and the flow of the fluid F1 in the pipe portion 48 is stopped while the fluid F1 is caused to flow into the pipe portion 47. The fluid F2 flows in the pipe portions 77 and 78. As a result, as illustrated in FIG. 12, only the aqueous solution as the liquid L1 flows through the flow channel 10 and the oily solution in the flow channel 10 is washed away. Accordingly, the aqueous solution is supplied to the flow channel 10 side of the communication hole 33 and the interface between the aqueous solution of the liquid L1 and the oily solution of the liquid L3 is formed in the communication hole 33. At the interface, a single molecule lipid membrane in which a hydrophilic group is arranged toward the aqueous solution side is formed in the communication hole 33. As in the case of the process S22, the aqueous solution and the oily solution as the liquids L3 and L4 flow in parallel in the flow channel 20.

The flow rate of the fluid F1 discharged by the pump unit 41 of the supply unit 40 and the flow rate of the fluid F2 discharged by the pump unit 71 of the supply unit 70 in the process S22 are maintained in the process S23. Since the valve 66 is closed and the flow of the fluid F1 in the pipe portion 48 is stopped, the flow rate of the fluid F1 in the pipe portion 47 increases by the flow rate of the fluid F1 flowing in the pipe portion 48 in the process S22. As a result, the flow rate of the aqueous solution flowing through the flow channel 10 increases by the flow rate of the oily solution flowing through the flow channel 10 in the process S22. Accordingly, a pressure change in the flow channel 10 is suppressed regardless of the switch from the process S22 to the process S23.

Subsequently, as illustrated in FIG. 10, the oily solution introduction into the flow channel 20 is stopped (process S24). Specifically, the valve 91 is closed and the flow of the fluid F2 in the pipe portion 77 is stopped while the fluid F2 is caused to flow into the pipe portion 78. The fluid F1 flows in the pipe portion 47. The flow of the fluid F1 in the pipe portion 48 is stopped. As a result, as illustrated in FIG. 13, only the aqueous solution as the liquid L4 flows into the flow channel 20 and the oily solution in the flow channel 20 is washed away. At this time, the hydrophobic group of a lipid β in the oily solution is disposed in the hydrophobic group of the single molecule lipid membrane formed in the communication hole 33 and a lipid bilayer membrane is formed in the communication hole 33. The formed lipid bilayer membrane has a structure in which the hydrophobic groups of two lipid molecules are oriented so as to face each other in a tail-to-tail manner.

The flow rate of the fluid F1 discharged by the pump unit 41 of the supply unit 40 and the flow rate of the fluid F2 discharged by the pump unit 71 of the supply unit 70 in the process S22 are maintained in the process S24. Since the valve 91 is closed and the flow of the fluid F2 in the pipe portion 77 is stopped, the flow rate of the fluid F2 in the pipe portion 78 increases by the flow rate of the fluid F2 flowing in the pipe portion 77 in the process S23. As a result, the flow rate of the aqueous solution flowing through the flow channel 20 increases by the flow rate of the oily solution flowing through the flow channel 20 in the process S23. Accordingly, a pressure change in the flow channel 20 is suppressed regardless of the switch from the process S23 to the process S24.

As described above, in the supply unit 40, the introduction unit 55 introduces the liquid L2 into the flow channel 10 at a flow rate corresponding to the flow rate of the fluid F1 flowing through the pipe portion 48. Accordingly, the introduction of the liquid L2 into the flow channel 10 is stopped by the flow of the fluid F1 in the pipe portion 48 being stopped. In a state where the flow of the fluid F1 in the pipe portion 48 is stopped, the fluid F1 discharged from the discharge port 41*a* of the pump unit 41 flows into a part of the branch pipe 45 other than the pipe portion 48. In the branch pipe 45, the pipe portions 47 and 48 branch off from the connecting portion 46, and thus the flow rate of the fluid F1 in the pipe portion 47 in the state where the flow of the fluid F1 in the pipe portion 48 is stopped increases as compared with a state where the flow of the fluid F1 in the pipe portion 48 is not stopped. In the embodiment and the modification example described above, the fluid F1 flows into the pipe portion 47 by the flow rate that does not flow into the pipe portion 48. The introduction unit 50 introduces the liquid L1 into the flow channel 10 at a flow rate corresponding to the flow rate of the fluid F1 flowing through the pipe portion 47. Accordingly, a change in the total flow rate of the liquids L1 and L2 flowing through the flow channel 10 is suppressed even in the case of transition between the state where the flow of the fluid F1 in the pipe portion 48 is stopped and the state where the flow of the fluid F1 in the pipe portion 48 is not stopped. Accordingly, in the liquid supply device 3, a change in pressure in the flow channel 10 is suppressed even in the case of transition between the state where the flow of the fluid F1 in the pipe portion 48 is stopped and the state where the flow of the fluid F1 in the pipe portion 48 is not stopped. As a result, it is possible to suppress a change in the pressure difference between the flow channel 10 and the flow channel 20 with a simple configuration and without electronically controlling the amounts of introduction of the liquids L1 and L2.

The supply unit 70 is similar in configuration to the supply unit 40. Accordingly, a change in pressure in the flow channel 20 is suppressed even in the case of transition between a state where the flow of the fluid F2 in the pipe portion 77 is stopped and a state where the flow of the fluid F2 in the pipe portion 77 is not stopped. As a result, it is possible to suppress a change in the pressure difference between the flow channel 10 and the flow channel 20 with a simple configuration and without electronically controlling the amounts of introduction of the liquids L1, L2, L3, and L4.

The introduction unit 50 includes the containing pipe 51 connected to the pipe portion 47 and containing the liquid L1. The introduction unit 55 includes the containing pipe 56 connected to the pipe portion 48 and containing the liquid L2. Accordingly, the liquid L1 contained in the containing pipe 51 is pushed out in accordance with the flow rate of the fluid F1 flowing through the pipe portion 47. The liquid L2 contained in the containing pipe 56 is pushed out in accordance with the flow rate of the fluid F1 flowing through the pipe portion 48. As a result, it is possible to suppress a change in the pressure difference between the flow channel 10 and the flow channel 20 with a simpler configuration.

The stopping portion 65 includes the valve 66 opening and closing the flow channel connecting the pipe portion 48 and the introduction unit 55. Accordingly, the flow of the fluid F1 in the pipe portion 48 can be easily stopped by the valve 66. Insofar as the valve 66 is provided between the introduction unit 55 and the pipe portion 48, the fluid F1 from the pump unit 41 flows into the pipe portion 47 without being affected by the compressibility of the liquid L2, flow channel expansion in the introduction unit 55, and so on when the flow of the fluid F1 of the pipe portion 48 is stopped by the valve 66. Accordingly, a change in pressure in the flow channel 10 is further suppressed.

The microfluidic device 2 has the inflow channels 11 and 12 connected to the flow channel 10. The inflow channels 11 and 12 are disposed at positions farther from the flow channel 20 than the communication hole 33 in the direction D2. The inflow channel 12 runs closer to the flow channel 20 side than the inflow channel 11 when viewed in the direction D3. The introduction unit 50 is disposed so as to introduce the liquid L1 into the inflow channel 11. The introduction unit 55 is disposed so as to introduce the liquid L2 into the inflow channel 12. In this case, a layer through which the liquid L1 flows and a layer through which the liquid L2 flows are formed in the flow channel 10 by the liquids L1 and L2 being introduced into the inflow channels 11 and 12, respectively. With this configuration, it is possible to control the liquid supplied to the communication hole 33 depending on whether or not the liquid L2 is introduced into the inflow channel 12.

The microfluidic device 2 has the inflow channels 21 and 22 connected to the flow channel 20. The inflow channels 21 and 22 are disposed at positions farther from the flow channel 10 than the communication hole 33 in the direction D2. The inflow channel 21 runs closer to the flow channel 10 side than the inflow channel 22 when viewed in the direction D3. The introduction unit 80 is disposed so as to introduce the liquid L3 into the inflow channel 21. The introduction unit 85 is disposed so as to introduce the liquid L4 into the inflow channel 22. In this case, a layer through which the liquid L3 flows and a layer through which the liquid L4 flows are formed in the flow channel 20 by the liquids L3 and L4 being introduced into the inflow channels 21 and 22, respectively. With this configuration, it is possible to control the liquid supplied to the communication hole 33 depending on whether or not the liquid L3 is introduced.

The diameter of the communication hole 33 is 1 to 15 µm. In this case, the cell α can be captured by the communication hole 33 by a pressure difference being provided between the flow channel 10 and the flow channel 20.

In the liquid supply method described above, the liquids L1 and L2 are introduced into the flow channel 10 in the step of causing the fluid to flow into the pipe portions 47 and 48. In the step of stopping the flow of the fluid F1 in the pipe portion 48, the liquid L1 is introduced into the flow channel 10 without the liquid L2 being introduced. In a state where the flow of the fluid F1 in the pipe portion 48 is stopped, the fluid F1 discharged from the discharge port 41a of the pump unit 41 flows into a part of the branch pipe 45 other than the pipe portion 48. Accordingly, the flow rate of the fluid F1 in the pipe portion 47 in the state where the flow of the fluid F1 in the pipe portion 48 is stopped increases as compared with a state where the flow of the fluid F1 in the pipe portion 48 is not stopped. Accordingly, in the liquid supply method described above, a change in pressure in the flow channel 10 is suppressed between the step of causing the fluid F1 to flow into the pipe portions 47 and 48 and the step of stopping the flow of the fluid F1 in the pipe portion 48. As a result, it is possible to suppress a change in the pressure difference between the flow channel 10 and the flow channel 20 with a simple configuration and without electronically controlling the amounts of introduction of the liquids L1 and L2.

In the step of causing the fluid to flow into the pipe portions 47 and 48, the liquid L1 and the liquid L2 are caused to flow in parallel such that the liquid L2 flows closer to the flow channel 20 than the liquid L1 in the flow channel 10. In this case, the liquid supplied to the communication hole 33 can be controlled between the step of causing the fluid F1 to flow into the pipe portions 47 and 48 and the step of stopping the flow of the fluid F1 in the pipe portion 48.

In the step of causing the fluid F2 to flow into the pipe portions 77 and 78, the liquids L3 and L4 are introduced into the flow channel 20. In the step of stopping the flow of the fluid F2 in the pipe portion 77, the liquid L4 is introduced into the flow channel 20 without the liquid L3 being introduced. Even in a state where the flow of the fluid in the pipe portion 77 is stopped, the fluid discharged from the discharge port 71a of the pump unit 71 flows into a part of the branch pipe 75 other than the pipe portion 77. Accordingly, the flow rate of the fluid F2 in the pipe portion 78 in the state where the flow of the fluid F2 in the pipe portion 77 is stopped increases as compared with a state where the flow of the fluid F2 in the pipe portion 77 is not stopped. Accordingly, in the liquid supply method described above, a change in pressure in the flow channel 20 is suppressed between the step of causing the fluid F2 to flow into the pipe portions 77 and 78 and the step of stopping the flow of the fluid F2 in the pipe portion 77. As a result, it is possible to suppress a change in the pressure difference between the flow channel 10 and the flow channel 20 with a simple configuration and without electronically controlling the amounts of introduction of the liquids L1, L2, L3, and L4.

In the step of causing the fluid F2 to flow into the pipe portions 77 and 78, the liquid L3 and the liquid L4 are caused to flow in parallel such that the liquid L3 flows closer to the flow channel 10 than the liquid L4 in the flow channel 20. In this case, the liquid supplied to the communication hole 33 can be controlled between the step of causing the fluid F2 to flow into the pipe portions 77 and 78 and the step of stopping the flow of the fluid F2 in the pipe portion 77.

In the embodiment described above, the liquid L2 is a suspension containing the plurality of cells α. The liquid L4 may be a sample containing a target substance to be brought into contact with the cell α. In the step of causing the fluid F1 to flow into the pipe portions 47 and 48 and the step of causing the fluid F2 to flow into the pipe portions 77 and 78, the fluids F1 and F2 are discharged from the pump unit 41 of the supply unit 40 and the pump unit 71 of the supply unit 70 such that the pressure in the flow channel 10 becomes higher than the pressure in the flow channel 20. The flow rate of the fluid F1 discharged by the pump unit 41 of the supply unit 40 and the flow rate of the fluid F2 discharged by the pump unit 71 of the supply unit 70 in the step of causing the fluid F1 to flow into the pipe portions 47 and 48 and the step of causing the fluid F2 to flow into the pipe portions 77 and 78 are maintained in the step of stopping the flow of the fluid F1 in the pipe portion 48.

In this case, the cell α can be captured on the flow channel 10 side of the communication hole 33. In the step of stopping the flow of the fluid F2 in the pipe portion 77, the target substance is capable of being brought into contact with the captured cell α. In the step of stopping the flow of the fluid F1 in the pipe portion 48, a change in the pressure difference between the flow channel 10 and the flow channel 20 is suppressed. Accordingly, the captured cell α is prevented from being unintentionally detached from the communication hole 33 and the captured cell a is prevented from being pressed against the communication hole 33 and crushed.

The flow rate of the fluid F1 discharged by the pump unit 41 of the supply unit 40 and the flow rate of the fluid F2 discharged by the pump unit 71 of the supply unit 70 in the step of causing the fluid F1 to flow into the pipe portions 47 and 48 and the step of causing the fluid F2 to flow into the pipe portions 77 and 78 are maintained in the step of stopping the flow of the fluid F2 in the pipe portion 77. In this case, a change in the pressure difference between the flow channel 10 and the flow channel 20 is suppressed in the step of stopping the flow of the fluid F2 in the pipe portion 77. Accordingly, the captured cell a is prevented from being unintentionally detached from the communication hole 33 and the captured cell α is prevented from being pressed against the communication hole 33 and crushed.

In the modification example described above, the liquid L4 is an aqueous solution. The liquid L3 is an oily solution in which the lipid β is dissolved. The liquid supply step includes a step of supplying the aqueous solution to the flow channel 10 before the step of stopping the flow of the fluid F2 in the pipe portion 77. In the step of causing the fluid F2 to flow into the pipe portions 77 and 78 and the step of supplying the aqueous solution to the flow channel 10, the fluid F1 and the fluid F2 are discharged from the pump unit 41 of the supply unit 40 and the pump unit 71 of the supply unit 70 such that the pressure in the flow channel 10 and the pressure in the flow channel 20 become equal to each other. The flow rate of the fluid F1 discharged by the pump unit 41 of the supply unit 40 and the flow rate of the fluid F2 discharged by the pump unit 71 of the supply unit 70 in the step of causing the fluid F2 to flow into the pipe portions 77 and 78 and the step of supplying the aqueous solution to the flow channel 10 are maintained in the step of stopping the flow of the fluid F2 in the pipe portion 77. In this case, a single molecule lipid membrane is formed in the communication hole 33 before the flow of the fluid F2 in the pipe portion 77 is stopped and a lipid bilayer membrane is formed in the communication hole 33 in the step of stopping the flow of the fluid F2 in the pipe portion 77. A change in the pressure difference between the flow channel 10 and the flow channel 20 is suppressed in the step of stopping the flow of the fluid F2 in the pipe portion 77. Accordingly, the formed lipid membrane is prevented from being crushed.

Although an embodiment and a modification example of the present invention have been described above, the present invention is not necessarily limited to the above-described embodiment and modification example. Various modifications can be made within the gist thereof.

For example, the shape of the communication portion 30 is not limited to the shapes described in the above-described embodiment and modification example. The communication portion 30 may include a slit allowing the flow channel 10 and the flow channel 20 to communicate with each other instead of the communication hole 33. In this case, "diameter of the communication hole 33" described in the embodiment and the modification example should be read as "slit width of the communication portion 30".

The number of the pipe portions branching off from the connecting portion 46 in the branch pipe 45 is not limited to two. The number of the pipe portions branching off from the connecting portion 76 in the branch pipe 75 is not limited to two. The liquid supply device 3 may be provided with introduction units connected to the pipe portions, the introduction units may be equal in number to the pipe portions of the branch pipes 45 and 75, and each pipe portion may be provided with a stopping portion.

The inflow channels 11, 12, 21, and 22 of the flow channels 10 and 20 are not limited to two in number. Three or more inflow channels may be connected to each of the flow channels 10 and 20.

The microfluidic device 2 may have a plurality of the communication portions 30 allowing the flow channel 10 and the flow channel 20 to communicate with each other.

The liquid supply device 3 may supply a liquid to only one of the flow channels 10 and 20. In this case, either the supply unit 40 or the supply unit 70 may not be used.

The fluids F1 and F2 discharged from the discharge ports 41a and 71a may be gases. The compressibility of a gas is greater than the compressibility of a liquid. Accordingly, when the fluids F1 and F2 discharged from the discharge ports 41a and 71a are liquids, the amounts of the liquids L1, L2, L3, and L4 supplied to the microfluidic device 2 as a result of the operation of the pump units 41 and 71 are adjusted with higher accuracy than when the fluids F1 and F2 are gases. In the above-described embodiment and modification example, the liquid supply device 3 is configured such that gas does not enter from the pump units 41 and 71 to the flow channels 10 and 20.

Various liquids may be disposed in the microfluidic device 2 before the fluids F1 and F2 are discharged from the pump unit 41 and the pump unit 71. For example, the liquid L1 may be disposed at a part of the inflow channel 11 and the flow channel 10, the liquid L2 may be disposed at a part of the inflow channel 12 and the flow channel 10, the liquid L3 may be disposed at a part of the inflow channel 21 and the flow channel 20, and the liquid L4 may be disposed at a part of the inflow channel 22 and the flow channel 20, before the operation of the pump unit 41 and the pump unit 71. In this case, the layer of the liquid L1 and the layer of the liquid L2 may be formed in advance in the flow channel 10. The layer of the liquid L3 and the layer of the liquid L4 may be formed in advance in the flow channel 20.

The introduction units 50, 55, 80, and 85 containing the liquids L1, L2, L3, and L4 are not limited to a tubular member directly connected to the branch pipes 45 and 75 as in the case of the containing pipes 51, 56, 81, and 86. For example, the introduction units 50, 55, 80, and 85 may be syringes discharging the respective liquids L1, L2, L3, and L4 with the pressure applied from the fluids F1 and F2 discharged from the pipe portions 47, 48, 77, and 78.

The supply unit 40 may lack the stopping portion 60. The supply unit 70 may lack the stopping portion 95.

The stopping portions 60, 65, 90, and 95 may be provided at one end or both ends of the containing pipes 51, 56, 81, and 86, respectively. The stopping portions 60, 65, 90, and 95 may be provided in the middle of the flow channels of the containing pipes 51, 56, 81, and 86, respectively.

The stopping portions 60, 65, 90, and 95 are not limited to a configuration stopping a fluid flow by means of a valve. For example, the stopping portions 60, 65, 90, and 95 may include an elastic tube instead of the valve and the elastic tube may constitute a part of the flow channel from the pipe portions 47, 48, 77, and 78 to the microfluidic device 2. The stopping portions 60, 65, 90, and 95 may be configured to close a part of the flow channel from the pipe portions 47, 48, 77, and 78 to the microfluidic device 2 by, for example, the elastic tube being bent manually.

REFERENCE SIGNS LIST

1: microdevice system, 2: microfluidic device, 3: liquid supply device, 10, 20: flow channel, 11, 12, 21, 22: inflow channel, 33: communication hole, 40, 70: supply unit, 41, 71: pump unit, 41a, 71a: discharge port, 45, 75: branch pipe, 46, 76: connecting portion, 47, 48, 77, 78: pipe portion, 50, 55, 80, 85: introduction unit, 51, 56, 81, 86: containing pipe, 60, 65, 90, 95: stopping portion, 61, 66, 91, 96: valve, F1, F2: fluid, L1, L2, L3, L4: liquid, D1, D2, D3: direction, α: cell, β: lipid.

The invention claimed is:

1. A liquid supply device comprising:
a pump unit comprising a single pump having a discharge port for discharging a fluid;
a branch pipe having a connecting portion connected to the discharge port and a first and a second pipe portion branching off from the connecting portion;
a first and a second introduction unit connected to the branch pipe, each of the first and second introduction units being arranged to supply a liquid to a microfluidic device having a first flow channel, a second flow channel running along the first flow channel, and a communication hole allowing the first flow channel and the second flow channel to communicate with each other; and
a stopping portion arranged to stop flow of the fluid in the second pipe portion, wherein
the first introduction unit is connected to the first pipe portion and is arranged to introduce a first liquid into the first flow channel at a first flow rate corresponding to a flow rate of the fluid flowing through the first pipe portion, the second introduction unit is connected to the second pipe portion and is arranged to introduce a second liquid into the first flow channel at a second flow rate corresponding to a flow rate of the fluid flowing through the second pipe portion, and
when the stopping portion switches from allowing to stopping flow of the fluid in the second pipe portion, a pressure change in the first flow channel is suppressed.

2. The liquid supply device according to claim 1, wherein the first introduction unit includes a first containing pipe connected to the first pipe portion and arranged to contain the first liquid inside, and
the second introduction unit includes a second containing pipe connected to the second pipe portion and arranged to contain the second liquid inside.

3. The liquid supply device according to claim 2, wherein the stopping portion includes a valve arranged to open and close a flow channel connecting the second pipe portion and the second introduction unit.

4. The liquid supply device according to claim 1, wherein the stopping portion includes a valve arranged to open and close a flow channel connecting the second pipe portion and the second introduction unit.

5. A microdevice system comprising:
a microfluidic device having a first flow channel, a second flow channel running along the first flow channel, and a communication hole allowing the first flow channel and the second flow channel to communicate with each other;
a first supply unit arranged to supply a liquid to the first flow channel; and
a second supply unit arranged to supply a liquid to the second flow channel,
wherein the first supply unit includes:
a pump unit comprising a single pump having a discharge port for discharging a fluid;
a branch pipe having a connecting portion connected to the discharge port of the pump unit of the first supply unit and a first and a second pipe portion branching off from the connecting portion;
a first introduction unit connected to the first pipe portion and arranged to introduce a first liquid into the first flow channel at a first flow rate corresponding to a flow rate of the fluid flowing through the first pipe portion;
a second introduction unit connected to the second pipe portion and arranged to introduce a second liquid into the first flow channel at a second flow rate corresponding to a flow rate of the fluid flowing through the second pipe portion; and
a stopping portion arranged to stop flow of the fluid in the second pipe portion, and
wherein when the stopping portion switches from allowing to stopping flow of the fluid in the second pipe portion, a pressure change in the first flow channel is suppressed.

6. The microdevice system according to claim 5, wherein the second supply unit includes:
a pump unit having a discharge port for discharging a fluid;
a branch pipe having a connecting portion connected to the discharge port of the pump unit of the second supply unit and a third and a fourth pipe portion branching off from the connecting portion;
a third introduction unit connected to the third pipe portion and arranged to introduce a third liquid into the second flow channel at a third flow rate corresponding to a flow rate of the fluid flowing through the third pipe portion;
a fourth introduction unit connected to the fourth pipe portion and arranged to introduce a fourth liquid into the second flow channel at a fourth flow rate corresponding to a flow rate of the fluid flowing through the fourth pipe portion; and a stopping portion arranged to stop the flow of the fluid in the third pipe portion.

7. The microdevice system according to claim 6, wherein the microfluidic device has third and fourth inflow channels connected to the second flow channel, the third and fourth inflow channels are disposed at positions farther from the first flow channel than the communication hole in a direction orthogonal to the extension direction of the second flow channel on a plane passing through the first flow channel and the second flow channel, the third inflow channel runs closer to the first flow channel side than the fourth inflow channel when viewed in a direction orthogonal to the plane, the third introduction unit is disposed so as to introduce the third liquid into the third inflow channel, and the fourth introduction unit is disposed so as to introduce the fourth liquid into the fourth inflow channel.

8. The microdevice system according to claim 6, wherein a diameter of the communication hole is 1 to 15 μm.

9. A microdevice system comprising:

a microfluidic device having a first flow channel, a second flow channel running along the first flow channel, and a communication hole allowing the first flow channel and the second flow channel to communicate with each other;

a first supply unit arranged to supply a liquid to the first flow channel; and a second supply unit arranged to supply a liquid to the second flow channel, wherein the first supply unit includes:

a pump unit having a discharge port for discharging a fluid;

a branch pipe having a connecting portion connected to the discharge port of the pump unit of the first supply unit and a first and a second pipe portion branching off from the connecting portion;

a first introduction unit connected to the first pipe portion and arranged to introduce a first liquid into the first flow channel at a first flow rate corresponding to a flow rate of the fluid flowing through the first pipe portion;

a second introduction unit connected to the second pipe portion and arranged to introduce a second liquid into the first flow channel at a second flow rate corresponding to a flow rate of the fluid flowing through the second pipe portion; and a stopping portion arranged to stop flow of the fluid in the second pipe portion, wherein the microfluidic device has first and second inflow channels connected to the first flow channel, the first and second inflow channels are disposed at positions farther from the second flow channel than the communication hole in a direction orthogonal to an extension direction of the second flow channel on a plane passing through the first flow channel and the second flow channel, the second inflow channel runs closer to the second flow channel side than the first inflow channel when viewed in a direction orthogonal to the plane, the first introduction unit is disposed so as to introduce the first liquid into the first inflow channel, and the second introduction unit is disposed so as to introduce the second liquid into the second inflow channel.

\* \* \* \* \*